(12) United States Patent
Ahmed

(10) Patent No.: US 11,426,369 B2
(45) Date of Patent: *Aug. 30, 2022

(54) COMPOSITIONS COMPRISING EPHEDRINE OR AN EPHEDRINE SALT AND METHODS OF MAKING AND USING SAME

(71) Applicant: Nexus Pharmaceuticals, Inc., Lincolnshire, IL (US)

(72) Inventor: Shahid Ahmed, Lincolnshire, IL (US)

(73) Assignee: Nexus Pharmaceuticals, Inc., Lincolnshire, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/556,904

(22) Filed: Dec. 20, 2021

(65) Prior Publication Data

US 2022/0110892 A1 Apr. 14, 2022

Related U.S. Application Data

(63) Continuation of application No. 17/381,770, filed on Jul. 21, 2021, which is a continuation of application No. 16/876,020, filed on May 16, 2020, now Pat. No. 11,090,278.

(60) Provisional application No. 62/849,125, filed on May 16, 2019.

(51) Int. Cl.
  *A61K 31/137* (2006.01)
  *A61K 9/00* (2006.01)

(52) U.S. Cl.
  CPC .......... *A61K 31/137* (2013.01); *A61K 9/0019* (2013.01)

(58) Field of Classification Search
  CPC ............................ A61K 31/137; A61K 9/0019
  See application file for complete search history.

(56) References Cited

U.S. PATENT DOCUMENTS

| | | | |
|---|---|---|---|
| 5,422,352 | A | 6/1995 | Astrup |
| 8,118,788 | B2 | 2/2012 | Frezza |
| 9,675,763 | B2 | 6/2017 | Huet |
| 10,869,845 | B1 | 12/2020 | Mohammed et al. |
| 11,052,186 | B2 | 7/2021 | Bonnefond et al. |
| 2005/0021092 | A1 | 1/2005 | Yun et al. |
| 2009/0024095 | A1 | 1/2009 | Frezza |
| 2013/0123289 | A1 | 5/2013 | Frezza |
| 2018/0140563 | A1 | 5/2018 | Thummar et al. |
| 2020/0315955 | A1 | 10/2020 | Soppimath et al. |
| 2021/0162141 | A1 | 6/2021 | Dody et al. |

FOREIGN PATENT DOCUMENTS

| | | |
|---|---|---|
| EP | 1919537 B1 | 8/2006 |
| EP | 2863968 B1 | 6/2013 |
| EP | 3484554 B1 | 6/2017 |
| WO | 2007/083034 A2 | 7/2007 |
| WO | 2012/022896 A1 | 2/2012 |
| WO | 2020/021201 A1 | 1/2020 |
| WO | 2020232424 A1 | 11/2020 |

OTHER PUBLICATIONS

Abdalla, Esam E.M., et al. "Ephedrine versus phenylephrine effects on fetal outcome and hemodynamics of pre-eclmaptic mothers undergoing cesarean section under spinal anesthesia," *Ain-Shams Journal of Anesthesiology*, 7: 215-20 (2014).
Adigun, T. A., et al. "Comparison of intravenous ephedrine with phenylephrine for the maintenance of arterial blood pressure during elective caesarean section under spinal anaesthesia," *Afr J Med Med Sci*, 39: 13-20 (2010).
Aguettant Ltd., "Ephedrine Hydrochloride 3 mg/ml Solution for Injection in Pre-filled Syringe: Summary of Product Characteristics," available at www.medicines.org.uk/emc/product/5354/smpc (Jun. 17, 2019).
Akers, "Sterile Drug Products: Formulation, Packaging, Manufacturing, and Quality," *Drugs and the Pharm. Sci.*, Swarbick, J, ed., Informa Healthcare (2010), 517 pages.
Akorn, Inc., Ephedrine Sulfate Injection product label (2012).
Am. Soc. Anesthesiologists, "Practice Guidelines for Obstetric Anesthesia: An Updated Report by the American Society of Anesthesiologists Task Force on Obstetric Anesthesia and the Society for Obstetric Anesthesia and Perinatology," *Anesthesiology*, 124: 270-300 (2016).
Ansel, H. *Pharmaceutical calculations* 13th edition Wolters Kluwer Health Lippincott Williams & Wilkins (2010).
Australian Government Department of Health, "Extract from the Clinical Evaluation Report for Ephedrine hydrochloride," Jun. 22, 2016 (44 pages).
Australian Government Department of Health, "Extract from the Clinical Evaluation Report for Ephedrine hydrochloride," Oct. 6, 2017 (28 pages).
Axelrod, J. "Studies on sympathomimetic amines. I. The biotransformation and physiological disposition of l-ephedrine and l-noreohedrine," *J Pharmacol Exp Ther*, 109:62-73 (1953).
Balcan, A., et al. "Spinal anaesthesia for caesarean section: Comparison of maternal and neonatal effects of bolus administration of ephedrine and phenylephrine," *European Journal of Anaesthesiology*, 28: 160 (2011).
Bedford Laboratories, Material safety data sheet, Ephedrine Sulfate Injection, USP (50mg/ml), (date unknown; downloaded Nov. 20, 2020), 4 pages.
Belzarena, S. D. "Ephedrine and etilefrine as vasopressor to correct maternal arterial hypotension during elective cesarean section under spinal anesthesia. Comparative study," *Rev Bras Anestesiol*, 56: 223-9 (2006).
Bhattarai, B., et al. "Comparison of bolus phenylephrine, ephedrine and mephentermine for maintenance of arterial pressure during spinal anesthesia in cesarean section," *JNMA J Nepal Med Assoc*, 49: 23-8 (2010).
Boakes, RJ, et al. "Actions of noradrenaline, other sympathomimetic amines and antagonists on neurones in the brain stem of the cat," *Br J Pharmacol* 41:462-479 (1971).
Boven, et al. "The increased incidence of pure red cell aplasia with an Eprex formulation in uncoated rubber stopper syringes," Kidney Int'l, vol. 67, pp. 2346-2353 (2005).

(Continued)

*Primary Examiner* — Shobha Kantamneni
(74) *Attorney, Agent, or Firm* — Incubate IP; Randy R. Micheletti

(57) ABSTRACT

The present disclosure provides compositions comprising ephedrine sulfate ready for immediate use in a clinical setting, and methods of making and using same.

9 Claims, No Drawings

(56) References Cited

OTHER PUBLICATIONS

Chen, K. "The Acute Toxicity of Ephedrine," *J Pharmacol Exp Ther* 27:61-76 (1926a).
Chen, K. "The Effect of Repeated Administration of Ephedrine," *J Pharmacol Exp Ther* 27:77-86 (1926b).
Chou, The Preparation and Properties of Ephedrine and Its Salts, J. Biol. Chem., vol. 70, pp. 109-114 (1926).
Clark, V. A., et al. "Ephedrine requirements are reduced during spinal anaesthesia for caesarean section in preeclampsia," *Int J Obstet Anesth*, 14: 9-13 (2005).
Cooper, D. W., et al. "Effect of intravenous vasopressor on spread of spinal anaesthesia and fetal acid-base equilibrium," *Br J Anaesth*, 98: 649-56 (2007).
Cooper, D. W., et al. "Fetal and maternal effects of phenylephrine and ephedrine during spinal anesthesia for cesarean delivery," *Anesthesiology*, 97: 1582-90 (2002).
Cox Gad, "Pharmaceutical Manufacturing Handbook: Production and Processes," Wiley-Interscience (2008), 1,386 pages.
Critchley, L. A., et al. "Hypotension during subarachnoid anaesthesia: haemodynamic effects of ephedrine," *Br J Anaesth*, 74: 373-8 (1995).
Datta, S., et al. "Method of ephedrine administration and nausea and hypotension during spinal anesthesia for cesarean section," *Anesthesiology*, 56: 68-70 (1982).
Desalu, I., et al. "Is ephedrine infusion more effective at preventing hypotension than traditional prehydration during spinal anaesthesia for caesarean section in African parturients?," *Inf J Obstet Anesth*, 14: 294-99 (2005).
Dhungana, Y., et al. "Prevention of hypotension during propofol induction: a comparison of preloading with 3.5% polymers of degraded gelatin (Haemaccel) and intravenous ephedrine," *Nepal Med Coll J*, 10: 16-9 (2008).
Diven, et al., "Extending Shelf Life Just Makes Sense," *Mayo Clin. Proc.*, vol. 90(11), pp. 1471-1474 (Nov. 2015), available at https://assets.documentcloud.org/documents/3677173/Extending-Shelf-Life-Just-Makes-Sense.pdf, 4 pages.
Dolci, M., et al. "Effect of an intravenous bolus of phenylephrine or ephedrine on skin blood flow during spinal anaesthesia: a randomised, double-blind, controlled study," *Eur J Anaesthesiol*, 28: 226-9 (2011).
Dulloo, AG, et al. "The thermogenic properties of ephedrine/methylxanthine mixtures: animal studies," *Am J Clin Nutr* 43:388-394 (1986).
ECLAT Pharmaceuticals, Akovaz(TM) Ephedrine Sulfate Injection product label (2016).
ECLAT Pharmaceuticals, Vazculep Package Insert (USA) In. (Jun. 2014).
Erkinaro, T., et al. "Divergent effects of ephedrine and phenylephrine on cardiovascular hemodynamics of near-term fetal sheep exposed to hypoxemia and maternal hypotension," *Acta Anaesthesiol Scand* 51:922-928 (2007).
Erkinaro, T., et al. "Effects of ephedrine and phenylephrine on uterine and placental circulations and fetal outcome following fetal hypoxaemia and epidural-induced hypotension in a sheep model," *Br J Anaesth* 93:825-832 (2004).
Erkinaro, T., et al. "Ephedrine and phenylephrine for the treatment of maternal hypotension in a chronic sheep model of increased placental vascular resistance," *Br J Anaesth* 96:231-237 (2006).
EXELA Pharma Sciences, LLC, Akovaz(TM) Ephedrine Sulfate Injection product label (Aug. 2021), 9 pages.
Fantoni, DT, et al. "Effect of ephedrine and phenylephrine on cardiopulmonary parameters in horses undergoing elective surgery," *Vet Anaesth Analg* 40:367-374 (2013).
Foss, V. T., et al. "Effect of phenylephrine vs. ephedrine on frontal lobe oxygenation during caesarean section with spinal anesthesia: an open label randomized controlled trial," *Front Physiol*, 5: 81 (2014).

Ganeshanavar, A., et al. "Comparison of bolus phenylephrine, ephedrine and mephentermine for maintenance of arterial pressure during spinal anaesthesia in caesarean section," *J Clin Diagn Res*, 5: 948-52 (2011).
Graham, BE, et al. "A pharmacologic study of ortho-methoxy-betaphenyl-Isopropyl methylamine hydrochloride, and 13 related methoxy analogues," *J Pharmacol Exp Ther* 94:150-166 (1948).
Griffiths et al., "The Stability of Ready-to-Use (RTU) Ephedrine Hydrochloride in Polypropylene Syringes for Use in Maternal Hypotension," *Eur. J. Hospital Pharm. Sci.*, vol. 11(5), pp. 107-110 (2005), 4 pages.
Gunda, C.P., et al. "Vasopressor choice for hypotension in elective Cesarean section: ephedrine or phenylephrine?," *Arch Med Sci*, 6: 257-63 (2010).
Hilliard, CA, et al. "Chromosome aberrations in vitro related to cytotoxicity of nonmutagenic chemicals and metabolic poisons" *Environ Mol Mutagen* 31:316-326 (1998).
Hoffman, B. "Catecholamines, Sympathomimetic Drugs, and Adrenergic Receptor Antagonist" in Goodman and Gilman's The Pharmacological Basis of Therapeutics (Hardman JaL, LE ed) pp. 215-268, McGraw-Hill Medical Publishing Division (2001).
ICH Harmonised Tripartite Guidelines, "Impurities of new drug products Q3B(R2)," (Jun. 2, 2006), 16 pages.
ICH Harmonised Tripartite Guidelines, "Validation of Analytical Procedures: Text and Methodology Q2 (R1)," (Nov. 2005), 17 pages.
Institute for Safe Medication Practices, ISMP Guidelines for Safe Preparation of Compounded Sterile Preparations (2016), 22 pages.
Iqbal, M.S., et al. "Optimal dose of prophylactic intravenous ephedrine for spinal-induced hypotension during cesarean section," *Anaesth Pain & Intensive Care*, 14: 71-75 (2010).
Ishiyama, T., et al. "Ephedrine, but not phenylephrine, increases bispectral index values during combined general and epidural anesthesia," *Anesth Analg*, 97: 780-4 (2003).
Jenke, "Extractables and leachables consideration for prefilled syringes," Expert Opinion on Drug Delivery, vol. 11(10), pp. 1591-1600 (2014), 11 pages.
Jenke, "Identification, analysis, and safety assessment of leachables and extractables," Trends Anal. Chem., vol. 101, pp. 56-65 (available online Nov. 11, 2017), 10 pages.
Kanai, TN, et al. "Cardiovascular teratogenicity of ephedrine in rats" (Abstract), p. 246, *Senten Ijo (Cong Anom)* (1986).
Kansal, A., et al. "Randomised trial of intravenous infusion of ephedrine or mephentermine for management of hypotension during spinal anaesthesia for Caesarean section," *Anaesthesia*, 60: 28-34 (2005).
Kasaba, T., et al. "Ephedrine, dopamine, or dobutamine to treat hypotension with propofol during epidural anesthesia," *Can J Anaesth*, 47: 237-41 (2000).
Kasahara, Y, "Antiinflammatory actions of ephedrines in acute inflammations," *Planta Med* 51:325-331 (1985).
Kitchen, C.C., et al. "Preserved frontal lobe oxygenation following calcium chloride for treatment of anesthesia-induced hypotension," *Front Physiol*, 5: 407 (2014).
Knoll AG, "(+)-Ephedrine as an Impurity in (−)-ephedrine hydrochloride—toxicological assessment," Jan. 20, 2000, 3 pages.
Kobayashi, S, et al. "The sympathomimetic actions of l-ephedrine and d-pseudoephedrine: direct receptor activation or norepinephrine release?" *Anesth Analg* 97:1239-1245 (2003).
Laboratoire Aguettant, "Ephedrine Hydrochloride 3 mg/ml Solution for Injection in Pre-filled Syringe," (Nov. 2, 2015), 10 pages.
Lecoq, J.P., et al. "Norepinephrine and ephedrine do not counteract the increase in cutaneous microcirculation induced by spinal anaesthesia," *Br J Anaesth*, 105: 214-19 (2010).
Liles, JT, et al. "Pressor responses to ephedrine are mediated by a direct mechanism in the rat," *J Pharmacol Exp Ther* 316:95-105 (2006).
Ma, et al., "Pharmacological Effects of Ephedrine Alkaloids on Human 1- and 2-Adrenergic Receptor Subtypes," *J. Pharm. Experimental Ther.* (Jul. 2007), (pp. 214-221.
Madsen J, et al. "Localization of thermogenesis induced by single infusion of ephedrine in dog," *Pharmacol Toxicol* 73:219-223 (1993).

(56) References Cited

OTHER PUBLICATIONS

Magalhaes, E., et al. "Ephedrine versus phenylephrine: prevention of hypotension during spinal block for cesarean section and effects on the fetus," *Rev Bras Anestesiol*, 59: 11-20 (2009).

Marvola, M. "Effect of acetylated derivatives of some sympathomimetic amines on the acute toxicity, locomotor activity and barbiturate anaesthesia time in mice," *Acta Pharmacol Toxicol (Copenh)* 38:474-489 (1976).

Marvola, M. et al. "Pharmacokinetics and locomotor activity increasing effect of ephedrine in mice," *Acta Pharmacol Toxicol (Copenh)* 43:381-386 (1978).

McGregor, DB, et al. "Reactivity of catecholamines and related substances in the mouse lymphoma L5178Y cell assay for mutagens," *Environ Mol Mutagen* 11:523-544 (1988).

Meersschaert, K., et al. "Terlipressin-ephedrine versus ephedrine to treat hypotension at the induction of anesthesia in patients chronically treated with angiotensin converting-enzyme inhibitors: a prospective, randomized, double-blinded, crossover study," *Anesth Analg*, 94: 835-40 (2002).

Meng, L. et al. "Effect of phenylephrine and ephedrine bolus treatment on cerebral oxygenation in anaesthetized patients," *British Journal of Anaesthesia*, 107, 209-17, (2011).

Meng, L., et al. "The impact of phenylephrine, ephedrine, and increased preload on third-generation Vigileo-FloTrac and esophageal doppler cardiac output measurements," *Anesth Analg*, 113: 751-57 (2011).

Meng, Y., et al. "Pharmacological effects of methamphetamine and other stimulants via inhalation exposure," *Drug Alcohol Depend* 53:111-120 (1999).

Miller, D.K., et al. "Repeated administration of ephedrine induces behavioral sensitization in rats," *Psychopharmacology (Berl)* 140:52-56 (1998).

Miller, D.K., et al. Sensitization of anorexia and locomotion induced by chronic administration of ephedrine in rats, *Life Sci* 65:501-511 (1999).

Millipore Sigma, "LiChrospher® 100 RP-8 and RP-8 Endcapped," available at https://www.emdmillipore.com/US/en/products/analytics-sample-prep/chromatography-for-analysis/analytical-hplc/lichrospher-hplc-columns-and-sorbents/lichrospher-100-rp-8-and-rp-8-endcapped/0g.b.qB.EdoAAAE_6hl3.Lxj,nav (accessed Nov. 19, 2020), 3 pages.

Miyagoshi, M., et al. "Antitussive effects of L-ephedrine, amygdalin, and makyokansekito (Chinese traditional medicine) using a cough model induced by sulfur dioxide gas in mice," *Planta Med* 275-278 (1986).

Moran, D.H., et al. "Phenylephrine in the prevention of hypotension following spinal anesthesia for cesarean delivery," *J Clin Anesth*, 3: 301-5 (1991).

Morishita, H., et al. "The vascular changes after ephedrine tachyphylaxis," *J Pharm Pharmacol*, 27: 574-9 (1975).

Ngan Kee, W.D., et al. "A dose response study of prophylactic intravenous ephedrine for the prevention of hypotension during spinal anesthesia for cesarean delivery," *Anesth Analg*, 90:1390-95 (2000).

Ngan Kee, W.D., et al. "A randomized double-blinded comparison of phenylephrine and ephedrine infusion combinations to maintain blood pressure during spinal anesthesia for cesarean delivery: the effects on fetal acid-base status and hemodynamic control," *Anesth Analg*, 107:1295-302 (2008).

Ngan Kee, W.D., et al. "Comparison of metaraminol and ephedrine infusions for maintaining arterial pressure during spinal anesthesia for elective cesarean section," *Anesthesiology*, 95:307-13 (2001).

Ngan Kee, W.D., et al. "Placental transfer and fetal metabolic effects of phenylephrine and ephedrine during spinal anesthesia for cesarean delivery," *Anesthesiology*, 111:506-12 (2009).

Ngan Kee, W.D., et al. "Randomised double-blinded comparison of phenylephrine vs ephedrine for maintaining blood pressure during spinal anaesthesia for non-elective Caesarean section," *Anaesthesia* 63:1319-26 (2008).

Niazi, "Handbook of Pharmaceutical Manufacturing Formulations: Sterile Products," vol. 6, CRC Press, LLC (2004), 363 pages.

Nishikawa, T., et al. "Cardiovascular teratogenicity of ephedrine in chick embryos," *Toxicol Lett* 29:59-63 (1985).

Nissen, P. et al. "Phenylephrine but not ephedrine reduces frontal lobe oxygenation following anesthesia-induced hypotension," *Neurocrit Care*; 12, 17-23 (2010).

NTP National Toxicology Program Toxicology and carcinogenesis studies of ephedrine sulfate (CAS No. 134-72-5) in F344/N rats and B6C3F1 mice (feed studies) in *Natl Toxicol Program Tech Rep Ser*, pp. 1-186 (1986).

Odagme M.T., et al. "Prophylactic Infusions of Phenylephrine and Ephedrine during Combined Spinal Epidural Anaesthesia for Caesarean Section: A Comparative Study," *Journal of Anesthesia & Clinical Research*, 4(9):357, DOI:10.4172/2155-6148.1000357 (2013).

PAR Pharmaceutical, Corphedra(TM) Ephedrine Sulfate Injection product label (2017), 8 pages.

PCT/US2020/033310, International Search Report & Written Opinion dated Aug. 17, 2020, 15 pages.

Pennekamp, C.W., et al. "Differential effect of phenylephrine and ephedrine on cerebral haemodynamics before carotid cross-clamping during carotid endarterectomy," *Br J Anaesth*, 109:831-33 (2012).

Prakash, S., et al. "Maternal and neonatal effects of bolus administration of ephedrine and phenylephrine during spinal anaesthesia for caesarean delivery: a randomised study," *Int J Obstet Anesth*, 19: 24-30 (2010).

Pubchem, Compound Summary, d-Ephedrine, available at https://pubchem.ncbi.nlm.nih.gov/compound/9457 (downloaded Oct. 30, 2020), 24 pages.

Pubchem, Ephedrine compound summary, available at https://pubchem.ncbi.nlm.nih.gov/compound/Ephedrine (last accessed Apr. 22, 2020), 65 pages.

Puri, N., et al. "Comparative Study of Ephedrine and Mephertermine in Treatment of Hypotension in Patients Undergoing Elective Trans Urethral Resection Prostate (TURP)," *Journal of Bangladesh College of Physicians and Surgeons*, 28: 10-16 (2010).

Radakovic, N., et al. "Evaluation of the effects of ephedrine on human lymphocytes in the comet assay," *Acta Veterinaria (Beograd)* 61:363-371 (2011).

Ralston, DH, et al. "Effects of equipotent ephedrine, metaraminol, mephentermine, and methoxamine on uterine blood flow in the pregnant ewe," *Anesthesiology* 40:354-370 (1974).

Ramanathan, S., et al. "Vasopressor therapy for hypotension due to epidural anesthesia for cesarean section," *Acta Anaesthesiol Scand*, 32: 559-65 (1988).

Ramsey, JJ, et al. "Energy expenditure, body composition, and glucose metabolism in lean and obese rhesus monkeys treated with ephedrine and caffeine," *Am J Clin Nutr* 68:42-51 (1998).

Rehman, A., et al. "Comparison of prophylactic ephedrine against prnephedrine during spinal anesthesia for caesarian sections," *Anaesthesia, Pain & Intensive Care*, 15 (2011).

Retzlaff, JA, et al. "Erythrocyte volume, plasma volume, and lean body mass in adult men and women," *Blood* 33:649-661 (1969).

Rice, et al., "Stereochemistry of ephedrine and its environmental significance: Exposure and effects directed approach," J. Hazardous Materials, vol. 348, pp. 39-46 (2018), 8 pages.

Sacha, et al., "Practical fundamentals of glass, rubber, and plastic sterile packaging systems," *Pharm. Dev. & Tech.*, vol. 15(1), pp. 6-34 (2010), DOI: 10.3109/10837450903511178, 29 pages.

Sacha, et al., "Pre-filled syringes: a review of the history, manufacturing and challenges," *Pharm. Dev. & Tech.*, vol. 20(1), pp. 1-11 (2015), DOI: 10.3109/10837450.2014.982825, 11 pages.

Sandoz Inc., Ephedrine Sulfate Injection USP, 50mg/mL Single-dose Vials approval letter (2017), 4 pages.

Saravanan, S., et al. "Equivalent dose of ephedrine and phenylephrine in the prevention of post-spinal hypotension in Caesarean section," *Br J Anaesth*, 96: 95-9 (2006).

Simin, A., et al. "Comparison the effect of ephedrine and phenylephrine in treatment of hypotension after spinal anesthesia during cesarean section," *Open Journal of Obstetrics and Gynecology*, 2: 192-96 (2012).

Sinsheimer, JE, et al. "Species differences in the metabolism of norephedrine in man, rabbit and rat," *Biochem J* 136:763-771 (1973).

(56) References Cited

OTHER PUBLICATIONS

Sintetica S.A., Ephedrine Sintetica (ephedrine hydrochloride) 50 mg/mL, available at sintetica.com/global/page/product/prod/41/concentration/21 (downloaded Jun. 28, 2021), 3 pages.

Sintetica S.A., Ephedrine Sintetica (ephedrine hydrochloride) 10 mg/mL, available at sintetica.com/global/page/product/prod/41/concentration/21 (downloaded Jun. 28, 2021), 3 pages.

Sintetica S.A., Ephedrine Sintetica (ephedrine hydrochloride) 5 mg/mL, available at sintetica.com/global/page/product/prod/53/concentration/33 (downloaded Jun. 28, 2021), 3 pages.

Storer, RD, et al. "Revalidation of the in vitro alkaline elution/rat hepatocyte assay for DNA damage: improved criteria for assessment of cytotoxicity and genotoxicity and results for 81 compounds," *Mutat Res* 368:59-101 (1996).

Storms, University of Georgia Dissertation Thesis, available at https://getd.libs.uga.edu/pdfs/storms_meredith_w_200205_phd.pdf (2002), 200 pages.

Szybalski, W. "Special microbiological systems. II. Observations on chemical mutagenesis in microorganisms," *Ann N Y Acad Sci* 76:475-489 (1958).

Taguchi, N., Tet al. "Hemodynamic effects of intravenous ephedrine in infants and children anesthetized with halothane and nitrous oxide," *Anesth Analg*, 82: 568-73 (1996).

Taivainen, T. "Comparison of ephedrine and etilefrine for the treatment of arterial hypotension during spinal anaesthesia in elderly patients," *Acta Anaesthesiol Scand*, 35: 164-9 (1991).

Thomas, D.G., et al. "Randomized trial of bolus phenylephrine or ephedrine for maintenance of arterial pressure during spinal anaesthesia for Caesarean section," *Br J Anaesth*, 76: 61-5 (1996).

Turkoz, A., et al. "Effectiveness of intravenous ephedrine infusion during spinal anaesthesia for caesarean section based on maternal hypotension, neonatal acid-base status and lactate levels," *Anaesth Intensive Care*, 30: 316-20 (2002).

U.S. Food & Drug Administration, CDER, "Administrative and Correspondence Documents," Application No. 208289Orig1s000 (Jan. 10, 2013), 184 pages.

U.S. Food & Drug Administration, CDER, "Chemistry Review(s)," Application No. 208289Orig1s000 (Aug. 18, 2015), 39 pages.

U.S. Food & Drug Administration, CDER, "Clinical Pharmacology and Biopharmaceutics Review(s)," Application No. 208289Orig1s000 (Aug. 26, 2015), 29 pages.

U.S. Food and Drug Administration, "Current FDA Perspective on Leachable Impurities in Parenteral and Ophthalmic Drug Products," David B. Lewis, Oct. 22-23, 2011, 27 pages.

U.S. Food and Drug Administration, "Guidance for Industry, Container Closure Systems for Packaging Human Drugs and Biologies," May 1999, 56 pages.

U.S. Food & Drug Administration, "Guidance for Industry: Sterile Drug Products Produced by Aseptic Processing—Current Good Manufacturing Practice," (Sep. 2004), 63 pages.

U.S. Food & Drug Administration, CDER, "Medical Review(s)," Application No. 208289Orig1s000 (Aug. 27, 2015), 153 pages.

U.S. Food & Drug Administration, CDER, "Other Review(s)," Application No. 208289Orig1s000 (Jul. 30, 2015), 135 pages.

U.S. Food & Drug Administration, CDER, "Pharmacology Review(s)," Application No. 208289Orig1s000 (Aug. 13, 2015), 48 pages.

U.S. Food and Drug Administration, "Question-based Review (QbR) for Sterility Assurance of Terminally Sterilized Products: Frequently Asked Questions," available at https://www.fda.gov/media/81734/download (Sep. 29, 2011), 38 pages.

U.S. Food & Drug Administration, CDER, "Summary Review," Application No. 208289Orig1s000 (Apr. 29, 2016), 27 pages.

U.S. Food & Drug Administration, CDER, Supplemental Approval Package for Akovaz ephedrine sulfate injection for intravenous use (Exela Pharma Sciences, LLC), Application No. 208289Orig1s006 (Aug. 2, 2021), 88 pages.

U.S. Food & Drug Administration, "Sterile Drug Process Inspections," available at https://www.gmp-compliance.org/guidelines/gmp-guideline/fda-program-7356-002a-sterile-drug-process-inspections (Sep. 11, 2015), 54 pages.

U.S. Pharmacopoeia, "<1664> Assesment of Drug Product Leachables Associated With Pharmaceutical Packagine/Delivery Systems," available at https://online.uspnf.com/uspnf/document/1_GUID-080B9CD2-A445-44A2-A529-2CC7F86BCC64_1_en-US (downloaded Jan. 28, 2020).

Vercauteren, M.P., et al. "Prevention of hypotension by a single 5-mg dose of ephedrine during small-dose spinal anesthesia in prehydrated cesarean delivery patients," *Anesth Analg*, 90:324-7 (2000).

Wellman, PJ, et al. "Effects of (−)-ephedrine on locomotion, feeding, and nucleus accumbens dopamine in rats," *Psychopharmacology (Berl)* 135:133-140 (1998).

West-Ward Pharmaceuticals, Phenylephrine Hydrochloride Package Insert (USA), In. (Dec. 2012).

Williams, R.C., J, et al. *Comparative metabolism of some amphetamines in various species*, Pergamon Press, New York, NY (1973).

Wright, P.M., et al. "Vasopressor therapy for hypotension during epidural anesthesia for cesarean section: effects on maternal and fetal flow velocity ratios," *Anesth Analg*, 75: 56-63 (1992).

Xu, B., et al. "Effects of ephedrine and phenylephrine on the correction of hypotension in the cesarean sections under subarachnoid anesthesia," *HealthMED*, 7: 2607-12 (2013).

Xue-Jun, Y., et al. "A study on the mutagenicity of 102 raw pharmaceuticals used in Chinese traditional medicine," *Mutat Res* 260:73-82 (1991).

Yin, X.J., et al. "A study on the mutagenicity of 102 raw pharmaceuticals used in Chinese traditional medicine," Mutat Res 260:73-82 (1991).

Yousefshahi, F., et al. "The Effect of Ephedrine on Fetal Outcome in Treatment of Maternal Hypotension Caused by Spinal Anesthesia During Cesarean Section," *Journal of Family and Reproductive Health*, 4:149-54 (2010).

Zeiger, E., et al. "*Salmonella* mutagenicity tests: IV. Results from the testing of 300 chemicals," *Environ Mol Mutagen* 11 Suppl 12:1-157 (1988).

COMPOSITIONS COMPRISING EPHEDRINE OR AN EPHEDRINE SALT AND METHODS OF MAKING AND USING SAME

PRIORITY CLAIMS AND CROSS-REFERENCE TO RELATED APPLICATIONS

This application is a continuation application of U.S. patent application Ser. No. 17/381,770, filed Jul. 21, 2021, which is a continuation application of U.S. patent application Ser. No. 16/876,020, filed May 16, 2020 and now issued as U.S. Pat. No. 11,090,278, which claims priority to U.S. Provisional Patent Application Ser. No. 62/849,125, filed May 16, 2019; and cross-references U.S. patent application Ser. No. 17/465,697, filed Sep. 2, 2021, which is a continuation application of U.S. patent application Ser. No. 17/381, 770, filed Jul. 21, 2021, the entire contents of each of which are incorporated herein by reference and relied upon.

BACKGROUND

Ephedrine sulfate ((1R,2S)-(−)-2-methylamine-1-phenyl-propan-1-ol sulfate) is an alpha- and beta-adrenergic agonist and a norepinephrine-releasing agent that is FDA-approved for the treatment of clinically important hypotension occurring in the setting of anesthesia. However, all FDA-approved formulations must be diluted ten-fold before administration to a patient.

Requiring dilution steps is inconvenient, delays administration of needed therapeutic intervention, and introduces a significant and dangerous source of potential error in the clinical setting. Dilution just before administration also introduces a significant risk of contamination to an otherwise sterile composition. For example, a recent study by the Institute for Safe Medicine Practices revealed that nearly 1 in 10 drug products are prepared incorrectly before dispensing to a patient. A 2009 survey reported that 30% of hospitals reported a patient event involving a compounding error in the previous 5-year period.

Shelf-stable ready-to-use formulations commonly include excipients, such as preservatives and/or chelating agents. The use of such agents, while advantageous from a stability perspective, prevents broad use of prediluted compositions due to risks of allergic reactions, patient sensitivities, and undesirable cross-reactivities with other medications. These risks are significant in certain settings, such as the emergency room, where quick action is required, often in the absence of complete patient records.

Typically, ephedrine sulfate compositions are prepared using aseptic compounding techniques, whether by a compounding lab or on-site by a medical professional. While generally considered to be safe, aseptic compounding still results in frequent (circa 1/1,000) contamination by biological materials. For example, Sandoz, US Compounding, Pharmakon Pharmaceuticals, Allergy Laboratories, Cantrell Drug Company, SCA Pharmaceuticals, Banner Pharmaceuticals and PherMEDium have recalled dozens of lots of compounded ephedrine sulfate, representing several million doses, for lack of sterility assurance since 2012. Current methods of administering ephedrine sulfate compositions therefore carry a serious infection risk to patients.

Ephedrine sulfate compositions are known to be susceptible to light, pH changes, and humidity. FDA-approved formulations have short shelf lives, typically about 24 months. Ready-to-use (e.g., prediluted) preparations of ephedrine sulfate are not known to be stable for more than 60 days; ready-to-use formulations of other ephedrine salts are not known to be stable for more than 12 months.

In view of these clinically relevant shortcomings, a need exists for improved formulations of ephedrine sulfate.

SUMMARY

The present disclosure provides formulations comprising ephedrine sulfate.

In some embodiments, the present disclosure provides compositions comprising ephedrine sulfate in water, wherein the ephedrine sulfate is present at a concentration of about 1 mg/mL to about 10 mg/mL.

In other embodiments, the present disclosure provides a sterile prediluted medicament comprising about 3.8 mg/mL of ephedrine or an equimolar amount of an ephedrine salt; about 9 mg/mL sodium chloride; and water.

In other embodiments, the present disclosure provides a packaged pharmaceutical product comprising a vial; and a solution housed within the vial, wherein the solution comprises, consists essentially of, or consists of about 5 mg/mL of ephedrine sulfate; about 9 mg/mL sodium chloride; and water.

In other embodiments, the present disclosure provides a method of administering ephedrine sulfate to a subject in need thereof, the method comprising drawing a composition comprising ephedrine sulfate from a sterile premixed pharmaceutical product into a syringe; and injecting the composition into the subject using the syringe, wherein the ephedrine sulfate is present in the composition in an amount of about 5 mg/mL.

In other embodiments, the present disclosure provides a method of making a ready-to-use pharmaceutical composition comprising ephedrine or an ephedrine salt, the method comprising combining ephedrine or an ephedrine salt, sodium chloride and water to provide a solution comprising about 3.8 mg/mL ephedrine or an equimolar amount of an ephedrine salt, and about 9 mg/mL sodium chloride; and thereafter sterilizing the solution to provide a ready-to-use pharmaceutical composition comprising ephedrine or an ephedrine salt.

These and other embodiments are described in further detail herein below.

The detailed description and examples provided herewith depict various embodiments of this disclosure for purposes of illustration only. One skilled in the art will readily recognize from the following discussion that alternative embodiments of the structures and methods illustrated herein may be employed without departing from the principles of embodiments described herein.

DETAILED DESCRIPTION

The present disclosure provides compositions (e.g., ready-to-use premixed pharmaceutical compositions) comprising ephedrine or an ephedrine salt that are ready for immediate use in a clinical setting.

The present disclosure is based in part on the inventor's discovery that pharmaceutical compositions consistent with those disclosed herein and comprising an ephedrine salt (e.g., ephedrine sulfate) in a premixed (e.g., ready-to-use) formulation that does not require reconstitution or dilution prior to administration to a subject remains stable and active after prolonged storage.

Ephedrine and Ephedrine Salts

Compositions of the present disclosure comprise ephedrine or a biologically active salt thereof.

Ephedrine has an empirical formula of $C_{10}H_{15}NO$, a molecular weight of 165.2 g/mol and a structural formula, in its clinically important 1R,2S enantiomer, as shown below:

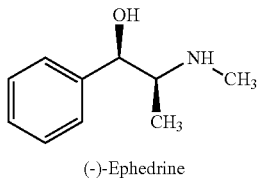

(-)-Ephedrine

Ephedrine sulfate has an empirical formula of $C_{20}H_{32}N_2O_6S$, a molecular weight of 428.5 g/mol and a structural formula, in its clinically important 1R,2S enantiomer, as shown below:

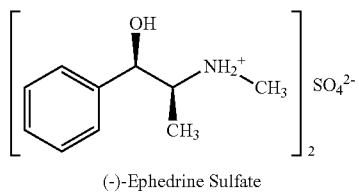

(-)-Ephedrine Sulfate

Ephedrine hydrochloride has an empirical formula of $C_{10}H_{16}NOCl$, a molecular weight of 201.7 g/mol and a structural formula, in its clinically important 1R,2S enantiomer, as shown below:

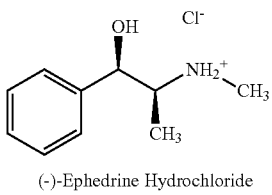

(-)-Ephedrine Hydrochloride

Ephedrine and its salts feature at least two chemically reactive centers, namely a secondary amine at C-2 and a secondary alcohol at C-1. In addition, ephedrine compositions are known to degrade during storage in a transparent container, including when contacted by light.

In some embodiments, a composition of the present disclosure comprises ephedrine. In some embodiments, the ephedrine is enantiopure (-)-ephedrine or substantially enantiopure (-)-ephedrine.

In some embodiments, after storage of a composition comprising enantiopure (-)-ephedrine or substantially enantiopure (-)-ephedrine at about 20° C. for at least 12 months, the composition comprises not more than about 30 wt. % (+)-ephedrine, for example not more than about 30 wt. %, not more than about 29 wt. %, not more than about 28 wt. %, not more than about 27 wt. %, not more than about 26 wt. %, not more than about 25 wt. %, not more than about 24 wt. %, not more than about 23 wt. %, not more than about 22 wt. %, not more than about 21 wt. %, not more than about 20 wt. %, not more than about 19 wt. %, not more than about 18 wt. %, not more than about 17 wt. %, not more than about 16 wt. %, not more than about 15 wt. %, not more than about 14 wt. %, not more than about 13 wt. %, not more than about 12 wt. %, not more than about 11 wt. %, not more than about 10 wt. %, not more than about 9 wt. %, not more than about 8 wt. %, not more than about 7 wt. %, not more than about 6 wt. %, not more than about 5 wt. %, not more than about 4 wt. %, not more than about 3 wt. %, not more than about 2 wt. %, not more than about 1 wt. % (+)-ephedrine.

In some embodiments, after storage of a composition comprising enantiopure (-)-ephedrine or substantially enantiopure (-)-ephedrine at about 20° C. for at least 24 months, the composition comprises not more than about 30 wt. % (+)-ephedrine, for example not more than about 30 wt. %, not more than about 29 wt. %, not more than about 28 wt. %, not more than about 27 wt. %, not more than about 26 wt. %, not more than about 25 wt. %, not more than about 24 wt. %, not more than about 23 wt. %, not more than about 22 wt. %, not more than about 21 wt. %, not more than about 20 wt. %, not more than about 19 wt. %, not more than about 18 wt. %, not more than about 17 wt. %, not more than about 16 wt. %, not more than about 15 wt. %, not more than about 14 wt. %, not more than about 13 wt. %, not more than about 12 wt. %, not more than about 11 wt. %, not more than about 10 wt. %, not more than about 9 wt. %, not more than about 8 wt. %, not more than about 7 wt. %, not more than about 6 wt. %, not more than about 5 wt. %, not more than about 4 wt. %, not more than about 3 wt. %, not more than about 2 wt. %, not more than about 1 wt. % (+)-ephedrine.

In some embodiments, a composition of the present disclosure comprises ephedrine sulfate. In some embodiments, the ephedrine sulfate is enantiopure (-)-ephedrine sulfate or substantially enantiopure (-)-ephedrine sulfate.

In some embodiments, after storage of a composition comprising enantiopure (-)-ephedrine sulfate or substantially enantiopure (-)-ephedrine sulfate at about 20° C. for at least 12 months, the composition comprises not more than about 30 wt. % (+)-ephedrine or salt thereof, for example not more than about 30 wt. %, not more than about 29 wt. %, not more than about 28 wt. %, not more than about 27 wt. %, not more than about 26 wt. %, not more than about 25 wt. %, not more than about 24 wt. %, not more than about 23 wt. %, not more than about 22 wt. %, not more than about 21 wt. %, not more than about 20 wt. %, not more than about 19 wt. %, not more than about 18 wt. %, not more than about 17 wt. %, not more than about 16 wt. %, not more than about 15 wt. %, not more than about 14 wt. %, not more than about 13 wt. %, not more than about 12 wt. %, not more than about 11 wt. %, not more than about 10 wt. %, not more than about 9 wt. %, not more than about 8 wt. %, not more than about 7 wt. %, not more than about 6 wt. %, not more than about 5 wt. %, not more than about 4 wt. %, not more than about 3 wt. %, not more than about 2 wt. %, not more than about 1 wt. % (+)-ephedrine or salt thereof.

In some embodiments, after storage of a composition comprising enantiopure (-)-ephedrine sulfate or substantially enantiopure (-)-ephedrine sulfate at about 20° C. for at least 24 months, the composition comprises not more than about 30 wt. % (+)-ephedrine or salt thereof, for example not more than about 30 wt. %, not more than about 29 wt. %, not more than about 28 wt. %, not more than about 27 wt. %, not more than about 26 wt. %, not more than about 25 wt. %, not more than about 24 wt. %, not more than about 23 wt. %, not more than about 22 wt. %, not more than about 21 wt. %, not more than about 20 wt. %, not more than about 19 wt. %, not more than about 18 wt. %, not more than about 17 wt. %, not more than about 16 wt. %, not more than about 15 wt. %, not more than about 14 wt. %, not more than about 13 wt. %, not more than about 12 wt. %, not more than about 11 wt. %, not more than about 10 wt. %, not more than about 9 wt. %, not more than about 8 wt. %, not more than about 7 wt. %, not more than about 6 wt. %, not more than about 5 wt. %, not more than about 4 wt. %, not more than about 3 wt. %, not more than about 2 wt. %, not more than about 1 wt. % (+)-ephedrine or salt thereof.

In some embodiments, a composition of the present disclosure comprises ephedrine hydrochloride. In some embodiments, the ephedrine hydrochloride is enantiopure (−)-ephedrine hydrochloride or substantially enantiopure (−)-ephedrine hydrochloride.

In some embodiments, after storage of a composition comprising enantiopure (−)-ephedrine hydrochloride or substantially enantiopure (−)-ephedrine hydrochloride at about 20° C. for at least 12 months, the composition comprises not more than about 30 wt. % (+)-ephedrine or salt thereof, for example not more than about 30 wt. %, not more than about 29 wt. %, not more than about 28 wt. %, not more than about 27 wt. %, not more than about 26 wt. %, not more than about 25 wt. %, not more than about 24 wt. %, not more than about 23 wt. %, not more than about 22 wt. %, not more than about 21 wt. %, not more than about 20 wt. %, not more than about 19 wt. %, not more than about 18 wt. %, not more than about 17 wt. %, not more than about 16 wt. %, not more than about 15 wt. %, not more than about 14 wt. %, not more than about 13 wt. %, not more than about 12 wt. %, not more than about 11 wt. %, not more than about 10 wt. %, not more than about 9 wt. %, not more than about 8 wt. %, not more than about 7 wt. %, not more than about 6 wt. %, not more than about 5 wt. %, not more than about 4 wt. %, not more than about 3 wt. %, not more than about 2 wt. %, not more than about 1 wt. % (+)-ephedrine or salt thereof.

In some embodiments, after storage of a composition comprising enantiopure (−)-ephedrine hydrochloride or substantially enantiopure (−)-ephedrine hydrochloride at about 20° C. for at least 24 months, the composition comprises not more than about 30 wt. % (+)-ephedrine or salt thereof, for example not more than about 30 wt. %, not more than about 29 wt. %, not more than about 28 wt. %, not more than about 27 wt. %, not more than about 26 wt. %, not more than about 25 wt. %, not more than about 24 wt. %, not more than about 23 wt. %, not more than about 22 wt. %, not more than about 21 wt. %, not more than about 20 wt. %, not more than about 19 wt. %, not more than about 18 wt. %, not more than about 17 wt. %, not more than about 16 wt. %, not more than about 15 wt. %, not more than about 14 wt. %, not more than about 13 wt. %, not more than about 12 wt. %, not more than about 11 wt. %, not more than about 10 wt. %, not more than about 9 wt. %, not more than about 8 wt. %, not more than about 7 wt. %, not more than about 6 wt. %, not more than about 5 wt. %, not more than about 4 wt. %, not more than about 3 wt. %, not more than about 2 wt. %, not more than about 1 wt. % (+)-ephedrine or salt thereof.

In some embodiments, a composition of the present disclosure comprises at least about 70% of the initial amount of (−)-ephedrine after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 80% of the initial amount of (−)-ephedrine after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 90% of the initial amount of (−)-ephedrine after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 95% of the initial amount of (−)-ephedrine after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 70% of the initial amount of (−)-ephedrine sulfate after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 80% of the initial amount of (−)-ephedrine sulfate after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 90% of the initial amount of (−)-ephedrine sulfate after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 95% of the initial amount of (−)-ephedrine sulfate after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 70% of the initial amount of (−)-ephedrine hydrochloride after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 80% of the initial amount of (−)-ephedrine hydrochloride after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 90% of the initial amount of (−)-ephedrine hydrochloride after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 95% of the initial amount of (−)-ephedrine hydrochloride after storage at about 20° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 70% of the initial amount of (−)-ephedrine after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 80% of the initial amount of (−)-ephedrine after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 90% of the initial amount of (−)-ephedrine after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 95% of the initial amount of (−)-ephedrine after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 70% of the initial amount of (−)-ephedrine sulfate after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 80% of the initial amount of (−)-ephedrine sulfate after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 90% of the initial amount of (−)-ephedrine sulfate after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 95% of the initial amount of (−)-ephedrine sulfate after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 70% of the initial amount of (−)-ephedrine hydrochloride after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 80% of the initial amount of (−)-ephedrine hydrochloride after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 90% of the initial amount of (−)-ephedrine hydrochloride after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure comprises at least about 95% of the initial amount of (−)-ephedrine hydrochloride after storage at about 40° C.+/−2° C. for at least about 12 months, for example at least about 12 months, at least about 14 months, at least about 16 months, at least about 18 months, at least about 20 months, at least about 22 months, at least about 24 months, at least about 26 months, at least about 28 months, at least about 30 months, at least about 32 months, at least about 34 months, at least about 36 months, at least about 38 months, at least about 40 months, at least about 42 months, at least about 44 months, at least about 46 months, at least about 48 months.

In some embodiments, a composition of the present disclosure includes not more than about 2 μg/mL of dichlorobenzoic acid after storage at about 25° C.+/−2° C. for at least about 12 months, for example not more than about 2 μg/mL, not more than about 1.9 μg/mL, not more than about 1.8 μg/mL, not more than about 1.7 μg/mL, not more than about 1.6 μg/mL, not more than about 1.5 μg/mL, not more than about 1.4 μg/mL, not more than about 1.3 μg/mL, not more than about 1.2 μg/mL, not more than about 1.1 μg/mL, not more than about 1 μg/mL, not more than about 0.9 μg/mL, not more than about 0.8 μg/mL, not more than about 0.7 μg/mL, not more than about 0.6 μg/mL, not more than about 0.5 μg/mL, not more than about 0.4 μg/mL, not more than about 0.3 μg/mL, not more than about 0.2 μg/mL, or not more than about 0.1 μg/mL.

In some embodiments, a composition of the present disclosure includes not more than about 2 μg/mL of dichlorobenzoic acid after storage at about 25° C.+/−2° C. for at least about 24 months, for example not more than about 2 μg/mL, not more than about 1.9 μg/mL, not more than about 1.8 μg/mL, not more than about 1.7 μg/mL, not more than about 1.6 μg/mL, not more than about 1.5 μg/mL, not more than about 1.4 μg/mL, not more than about 1.3 μg/mL, not more than about 1.2 μg/mL, not more than about 1.1 μg/mL, not more than about 1 μg/mL, not more than about 0.9 μg/mL, not more than about 0.8 μg/mL, not more than about 0.7 μg/mL, not more than about 0.6 μg/mL, not more than about 0.5 μg/mL, not more than about 0.4 μg/mL, not more than about 0.3 μg/mL, not more than about 0.2 μg/mL, or not more than about 0.1 μg/mL.

Ready-to-Use Ephedrine Formulations

In some embodiments, a composition of the present disclosure comprises ephedrine or an ephedrine salt, an isotonic agent, and water.

In some embodiments, a composition of the present disclosure does not include a preservative. Non-limiting examples of preservatives include (e.g., benzyl alcohol, chlorobutanol, phenyl ethyl alcohol), parabens (e.g., methylparaben, ethylparaben, propylparaben, butylparaben), phenols (e.g., phenol, chlorocresol, o-phenyl phenol), mercurial compounds (e.g., thiomersal, nitromersol, phenylmercuric nitrate, phenylmercuric acetate), and quaternary ammonium compounds (e.g., benzalkonium chloride, cetyl pyridinium chloride). In some embodiments, the composition does not include benzyl alcohol.

In some embodiments, a composition of the present disclosure does not include a chelating agent. Non-limiting examples of chelating agents include EDTA, calcium disodium edetate, and disodium edetate. In some embodiments, the composition does not include EDTA.

In some embodiments, the composition does not include a preservative or a chelating agent. In some embodiments, the composition does not include benzyl alcohol or EDTA.

In some embodiments, the ephedrine or ephedrine salt is present in an amount equivalent to about 3.8 mg/mL of ephedrine free base. For example and without limitation, embodiments in which the ephedrine or the ephedrine salt consists of ephedrine free base, the ephedrine free base may be present in an amount of about 3.8 mg/mL. In embodiments wherein the ephedrine or the ephedrine salt consists of ephedrine sulfate, the ephedrine sulfate may be present in an amount of about 5 mg/mL. In embodiments wherein the ephedrine or the ephedrine salt consists of ephedrine hydrochloride, the ephedrine hydrochloride may be present in an amount of about 4.6 mg/mL.

In some embodiments, the isotonic agent is sodium chloride. In other embodiments, the isotonic agent is dextrose. In embodiments in which the isotonic agent is sodium chloride, the sodium chloride may be present in an isotonic amount, such as about 9 mg/mL. In embodiments in which the isotonic agent is dextrose, the sodium chloride may be present in an isotonic amount, such as about 5%.

In some embodiments, a composition of the present disclosure comprises ephedrine (e.g., (−)-ephedrine), sodium chloride and water (e.g., water for injection). In some embodiments, the ephedrine is present in an amount of about 3.8 mg/mL, and the sodium chloride is present in an amount of about 9 mg/mL.

In some embodiments, a composition of the present disclosure comprises ephedrine sulfate (e.g., (−)-ephedrine sulfate), sodium chloride and water (e.g., water for injection). In some embodiments, the ephedrine sulfate is present in an amount of about 5 mg/mL, and the sodium chloride is present in an amount of about 9 mg/mL.

In some embodiments, a composition of the present disclosure comprises ephedrine hydrochloride (e.g., (−)-ephedrine hydrochloride), sodium chloride and water (e.g., water for injection). In some embodiments, the ephedrine hydrochloride is present in an amount of about 4.6 mg/mL, and the sodium chloride is present in an amount of about 9 mg/mL.

In some embodiments, a composition of the present disclosure comprises ephedrine (e.g., (−)-ephedrine), dextrose and water (e.g., water for injection). In some embodiments, the ephedrine is present in an amount of about 3.8 mg/mL, and the dextrose is present in an amount of about 5%.

In some embodiments, a composition of the present disclosure comprises ephedrine sulfate (e.g., (−)-ephedrine sulfate), dextrose and water (e.g., water for injection). In some embodiments, the ephedrine sulfate is present in an amount of about 5 mg/mL, and the dextrose is present in an amount of about 5%.

In some embodiments, a composition of the present disclosure comprises ephedrine hydrochloride (e.g., (−)-ephedrine hydrochloride), dextrose and water (e.g., water for injection). In some embodiments, the ephedrine hydrochloride is present in an amount of about 4.6 mg/mL, and the dextrose is present in an amount of about 5%.

In any embodiment disclosed herein, the composition may have a total volume sufficient to provide an efficacious dose of ephedrine to a subject. In some embodiments, the total volume is about 5 mL to about 25 mL, for example about 5 mL, about 10 mL, about 15 mL, about 20 mL, or about 25 mL. In some embodiments, the total volume is about 10 mL.

In any embodiment disclosed herein, the composition may be housed within a container, such as a single-use container. In some embodiments, the single-use container is a vial, such as a glass vial. In other embodiments, the single-use container is a syringe, such as a polypropylene syringe.

In some embodiments, the present disclosure provides a single-use container comprising about 10 mL of a composition comprising about 38 mg of ephedrine (e.g., (−)-ephedrine), about 90 mg of sodium chloride, and water (e.g., water for injection). In some embodiments, the single-use container is a glass vial. In some embodiments, the single-use container is a syringe.

In some embodiments, the present disclosure provides a single-use container comprising about 10 mL of a composition comprising about 50 mg of ephedrine sulfate (e.g., (−)-ephedrine sulfate), about 90 mg of sodium chloride, and water (e.g., water for injection). In some embodiments, the single-use container is a glass vial. In some embodiments, the single-use container is a syringe.

In some embodiments, the present disclosure provides a single-use container comprising about 10 mL of a composition comprising about 46 mg of ephedrine hydrochloride (e.g., (−)-ephedrine hydrochloride), about 90 mg of sodium chloride, and water (e.g., water for injection). In some embodiments, the single-use container is a glass vial. In some embodiments, the single-use container is a syringe.

In some embodiments, the present disclosure provides a shelf-stable composition comprising ephedrine or an ephedrine salt (e.g., ephedrine sulfate) that does not include a preservative, such as benzyl alcohol. In some embodiments, the shelf-stable composition comprises ephedrine or an ephedrine salt (e.g., ephedrine sulfate), an isotonic agent (e.g., sodium chloride) and water, but does not include a preservative (e.g., benzyl alcohol). In some embodiments, the shelf-stable composition comprises ephedrine sulfate (e.g., (−)-ephedrine sulfate), sodium chloride and water, but does not include benzyl alcohol.

In some embodiments, the present disclosure provides a shelf-stable composition comprising ephedrine or an ephedrine salt (e.g., ephedrine sulfate) that does not include a chelating agent, such as EDTA. In some embodiments, the shelf-stable composition comprises ephedrine or an ephedrine salt (e.g., ephedrine sulfate), an isotonic agent (e.g., sodium chloride) and water, but does not include a chelating agent (e.g., EDTA). In some embodiments, the shelf-stable composition comprises ephedrine sulfate (e.g., (−)-ephedrine sulfate), sodium chloride and water, but does not include EDTA.

In some embodiments, the present disclosure provides a shelf-stable composition comprising ephedrine or an ephedrine salt (e.g., ephedrine sulfate) that does not include a preservative (e.g., benzyl alcohol) or a chelating agent (e.g., EDTA). In some embodiments, the shelf-stable composition comprises ephedrine or an ephedrine salt (e.g., ephedrine sulfate), an isotonic agent (e.g., sodium chloride) and water, but does not include a preservative (e.g., benzyl alcohol) or a chelating agent (e.g., EDTA). In some embodiments, the shelf-stable composition comprises ephedrine sulfate (e.g., (−)-ephedrine sulfate), sodium chloride and water, but does not include benzyl alcohol or EDTA.

In some embodiments, a composition of the present disclosure has a pH value of 4.5 to 7.0. In some embodiments, the composition has a pH value of 5.5 to 6.5. In some embodiments, the composition has a pH value of about 5.6 to 6.2. In some embodiments, the composition has a pH value of about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, or about 7.0.

In some embodiments, a composition of the present disclosure includes no more than 10 colony forming units ("CFU") per mL, for example no more than 10 CFU/mL, no more than 9 CFU/mL, no more than 8 CFU/mL, no more than 7 CFU/mL, no more than 6 CFU/mL, no more than 5 CFU/mL, no more than 4 CFU/mL, no more than 3 CFU/mL, no more than 2 CFU/mL, no more than 1 CFU/mL, no more than 0.5 CFU/mL, no more than 0.4 CFU/mL, no more than 0.3 CFU/mL, no more than 0.2 CFU/mL, or no more than 0.1 CFU/mL.

In some embodiments, a composition of the present disclosure includes bacterial endotoxins in an amount of no more than 1.7 Eu/mg, no more than 1.6 Eu/mg, no more than 1.5 Eu/mg, no more than 1.4 Eu/mg, no more than 1.3 Eu/mg, no more than 1.2 Eu/mg, no more than 1.1 Eu/mg, no more than 1.0 Eu/mg, no more than 0.9 Eu/mg, no more than 0.8 Eu/mg, no more than 0.7 Eu/mg, no more than 0.6 Eu/mg, no more than 0.5 Eu/mg, no more than 0.4 Eu/mg, no more than 0.3 Eu/mg, no more than 0.2 Eu/mg, or no more than 0.1 Eu/mg.

In some embodiments, the present disclosure provides a composition comprising ephedrine sulfate in water, wherein the ephedrine sulfate is present at a concentration of about 1 mg/mL to about 10 mg/mL. In some embodiments, the ephedrine sulfate is present at a concentration of about 2 mg/mL to about 8 mg/mL. In some embodiments, the ephedrine sulfate is present at a concentration of about 3 mg/mL to about 7 mg/mL. In some embodiments, the ephedrine sulfate is present at a concentration of about 4 mg/mL to about 6 mg/mL. In some embodiments, the ephedrine sulfate is present at a concentration of about 5 mg/mL. In some embodiments, the composition further comprises sodium chloride. In some embodiments, the sodium chloride is present in an amount of about 9 mg/mL. In some embodiments, the composition is stable when stored at 20° C. for at least 12 months. In some embodiments, the composition does not include dextrose. In some embodiments, the composition does not include a preservative such as benzyl alcohol. In some embodiments, the composition does not include a chelating agent such as EDTA. In some embodiments, the composition consists essentially of ephedrine sulfate, sodium chloride and water. In some embodiments, the composition consists of ephedrine sulfate, sodium chloride and water. In some embodiments, the ephedrine sulfate is (−)-ephedrine sulfate.

In some embodiments, the present disclosure provides a sterile prediluted medicament comprising about 3.8 mg/mL of ephedrine or an equimolar amount of an ephedrine salt; about 9 mg/mL sodium chloride; and water. In some embodiments, the medicament does not include dextrose. In some embodiments, the medicament does not include benzyl alcohol. In some embodiments, a total volume of the medicament is about 10 mL. In some embodiments, the medicament is housed in a vial. In some embodiments, after storage at about 20° C., the medicament comprises at least 3 mg/mL of the ephedrine or a molar equivalent of the ephedrine salt. In some embodiments, the ephedrine or ephedrine salt is ephedrine sulfate. In some embodiments, the ephedrine sulfate is (−)-ephedrine sulfate.

In some embodiments, the present disclosure provides a ready-to-use unit dose form comprising about 3.8 mg/mL of ephedrine or an equimolar amount of an ephedrine salt (e.g., about 5 mg/mL of ephedrine sulfate); about 9 mg/mL of sodium chloride; and water. In some embodiments, the ready-to-use unit dose form is housed in a vial. In some embodiments, the ready-to-use unit dose form has a total volume of about 10 mL. In some embodiments, the ready-to-use unit dose form does not include dextrose. In some embodiments, the ready-to-use unit dose form does not include benzyl alcohol. In some embodiments, after storage at about 20° C., the ready-to-use unit dose form comprises at least 3 mg/mL of the ephedrine or an equimolar amount of the ephedrine salt (e.g., at least 4 mg/mL of ephedrine sulfate).

In some embodiments, the present disclosure provides a packaged pharmaceutical product comprising a vial; and a solution housed within the vial, wherein the solution comprises, consists essentially of, or consists of about 5 mg/mL of ephedrine sulfate; about 9 mg/mL sodium chloride; and water. In some embodiments, the solution has a total volume of about 10 mL. In some embodiments, the solution does not include dextrose. In some embodiments, the vial comprises, consists essentially of, or consists of glass. In some embodiments, the vial comprises, consists essentially of, or consists of polypropylene. In some embodiments, the solution is stable when stored at about 20° C. for at least 12 months. In some embodiments, after storage at about 20° C. for at least 12 months, the solution comprises ephedrine sulfate at a concentration of about 4 mg/mL to about 6 mg/mL. In some embodiments, after storage at about 20° C. for at least 12 months, the solution comprises at least 4 mg/mL of ephedrine sulfate. In some embodiments, after storage at about 20° C. for at least 12 months, the solution comprises at least 4.5 mg/mL ephedrine sulfate. In some embodiments, the ephedrine sulfate is (−)-ephedrine sulfate.

Methods of Using Ready-to-Use Ephedrine Compositions

The present disclosure provides methods of using ready-to-use compositions comprising ephedrine or an ephedrine salt. Generally, the methods disclosed herein do not require a clinician to dilute the ready-to-use composition before administering the ready-to-use composition to a subject. In some embodiments, the risk of microbial contamination to the subject is lower, such as substantially lower, when administered ready-to-use ephedrine compositions consistent with the present disclosure compared to the risk of microbial contamination to subjects (e.g., similarly situated subjects) who are administered ephedrine compositions that require dilution of a concentrated packaged ephedrine pharmaceutical composition.

In some embodiments, the present disclosure provides a method of reducing a risk of microbial infection associated with administration of ephedrine or an ephedrine salt (e.g., ephedrine sulfate) to a subject in need thereof.

In some embodiments, a risk of microbial contamination to a subject administered a ready-to-use composition comprising ephedrine or an ephedrine salt (e.g., ephedrine sulfate) consistent with the present disclosure is lower, or substantially lower, than a risk of microbial contamination to a second subject administered ephedrine sulfate diluted (e.g., diluted by a clinician) to a concentration of 5 mg/mL. In some such embodiments, the second subject receives ephedrine sulfate prepared by mixing (e.g., diluting) a concentrated ephedrine sulfate composition from a sterilized packaged pharmaceutical product comprising 50 mg/mL ephedrine sulfate with a diluent, such as saline, to form the diluted ephedrine sulfate composition.

In some embodiments, the present disclosure provides a method of administering ephedrine sulfate to a subject in need thereof, the method comprising drawing a composition comprising ephedrine sulfate from a sterile premixed pharmaceutical product into a syringe; and injecting the composition into the subject using the syringe, wherein the ephedrine sulfate is present in the composition in an amount of about 5 mg/mL. In some embodiments, the composition further comprises sodium chloride in an amount of about 9 mg/mL. In some embodiments, the composition further comprises water. In some embodiments, the composition does not include dextrose. In some embodiments, the method does not include diluting the sterile premixed pharmaceutical product before the step of injecting the composition into the subject using the syringe. In some embodiments, the composition housed within the vial of the sterile premixed pharmaceutical product is stable when stored at about 20° C. for at least 12 months. In some embodiments, after storage at about 20° C. for at least 12 months, the composition comprises ephedrine sulfate in an amount of about 4 mg/mL to about 6 mg/mL. In some embodiments, the ephedrine sulfate is (−)-ephedrine sulfate.

In some embodiments, the present disclosure provides a method of treating hypotension in a subject in need thereof, the method comprising drawing an effective amount of a packaged composition comprising ephedrine or an ephedrine salt into a syringe; and injecting the effective amount of the packaged composition into the subject in need thereof. In some embodiments, the packaged composition comprises ephedrine or an ephedrine salt in an amount equivalent to about 3.8 mg/mL ephedrine. In some embodiments, the packaged composition further comprises sodium chloride in an amount of about 9 mg/mL. In some embodiments, the packaged composition further comprises water. In some embodiments, the packaged composition does not include dextrose. In some embodiments, the method does not include diluting the packaged composition before the step of injecting the effective amount of the packaged composition into the subject in need thereof. In some embodiments, the packaged composition is stable when stored at about 20° C. for at least 12 months. In some embodiments, after storage at about 20° C. for at least 12 months, the packaged composition comprises ephedrine sulfate in an amount of about 4 mg/mL to about 6 mg/mL. In some embodiments, the ephedrine or ephedrine salt is (−)-ephedrine sulfate. In some embodiments, the method further comprises determining a low blood pressure reading in the subject before the step of drawing the effective amount of the packaged composition comprising ephedrine or an ephedrine salt into the syringe. In some embodiments, the hypotension is clinically important hypotension. In some embodiments, the clinically important hypotension is clinically important hypotension in the setting of anesthesia. In some embodiments, the method further comprises detecting a hypotensive state (e.g., a clinically important hypotensive state) associated with the subject before injecting the effective amount of the packaged composition into the subject.

In some embodiments, the present disclosure provides a method of increasing a blood pressure in a subject in need thereof, the method comprising determining a low blood pressure reading associated with a subject; drawing about 1 mL to about 10 mL of a packaged composition comprising about 5.0 mg/mL ephedrine sulfate into a syringe; injecting about 1 mL to about 10 mL of the packaged composition into the subject in need thereof, wherein the blood pressure reading associated with the subject increases after the step of injecting the packaged composition into the subject in need thereof, and wherein the method does not include diluting the packaged composition before the step of injecting the packaged composition into the subject in need thereof. In some embodiments, the packaged composition further comprises sodium chloride in an amount of about 9 mg/mL. In some embodiments, the packaged composition further comprises water. In some embodiments, the packaged composition does not include dextrose. In some embodiments, the method further comprises determining a second blood pressure reading associated with the subject after the step of injecting the packaged composition into the subject, wherein the second blood pressure reading is hypotensive. In some embodiments, the method further comprises injecting about 1 mL to about 10 mL of the packaged composition into the subject after the step of determining the second hypotensive blood pressure reading associated with the subject. In some embodiments, the packaged composition is stable when stored at about 20° C. for at least 12 months. In some embodiments, after storage at about 20° C. for at least 12 months, the packaged composition comprises ephedrine sulfate in an amount of at least about 4 mg/mL. In some embodiments, after storage at about 20° C. for at least 12 months, the packaged composition comprises ephedrine sulfate in an amount of at least about 4.5 mg/mL. In some embodiments, the ephedrine sulfate is (−)-ephedrine sulfate.

Methods of Making Ready-to-Use Ephedrine Compositions

The present disclosure further provides methods of making ready-to-use compositions comprising ephedrine or an ephedrine salt.

In general terms, ephedrine or an ephedrine salt (e.g., ephedrine sulfate) is combined with sodium chloride or dextrose in water for injection and mixed to form a clear, colorless solution. In some embodiments, the pH of the solution is adjusted to 4.5 to 7.0 using an acid (e.g., glacial acetic acid) or a base (e.g., sodium hydroxide). The final concentration of ephedrine or the ephedrine salt in the optionally pH-adjusted solution is equivalent to about 3.8 mg/mL of ephedrine free base. Accordingly, in embodiments wherein the ephedrine or the ephedrine salt is ephedrine sulfate, the final concentration of ephedrine sulfate in the optionally pH-adjusted solution is about 5.0 mg/mL. In embodiments wherein the ephedrine or the ephedrine salt is ephedrine hydrochloride, the final concentration of ephedrine hydrochloride in the optionally pH-adjusted solution is about 4.6 mg/mL. The concentration of sodium chloride or dextrose in the optionally pH-adjusted solution should be isotonic to human serum (e.g., about 9 mg/mL sodium chloride or about 5% dextrose).

The ephedrine or ephedrine salt solution must be sterilized before use by a clinician. In some embodiments, the ephedrine or ephedrine salt solution is placed in vials (e.g., glass or plastic single-use vials) and then sterilized by any suitable method known in the art.

In some embodiments, the present disclosure provides a method of making a ready-to-use pharmaceutical composition comprising ephedrine or an ephedrine salt, the method comprising combining ephedrine or an ephedrine salt, sodium chloride and water to provide a solution comprising about 3.8 mg/mL ephedrine or an equimolar amount of an ephedrine salt, and about 9 mg/mL sodium chloride; and thereafter sterilizing the solution to provide a ready-to-use pharmaceutical composition comprising ephedrine or an ephedrine salt. In some embodiments, the method further comprises placing the solution in one or more vials before the step of sterilizing. In some embodiments, the solution does not include dextrose. In some embodiments, the pharmaceutical composition is stable when stored at about 20° C. for at least 12 months. In some embodiments, after storage at about 20° C. for at least 12 months, the pharmaceutical composition comprises an amount of the ephedrine or the ephedrine salt that is at least 80% of the about 3.8 mg/mL ephedrine or the equimolar amount of the ephedrine salt.

In some embodiments, the ephedrine or the ephedrine salt is ephedrine sulfate. In some embodiments, the ephedrine salt is (−)-ephedrine sulfate. In some embodiments, the equimolar amount of the ephedrine salt is about 5 mg/mL of the ephedrine sulfate. In some embodiments, the ephedrine or the ephedrine salt is ephedrine hydrochloride. In some embodiments, the ephedrine hydrochloride is (−)-ephedrine hydrochloride. In some embodiments, the equimolar amount of the ephedrine salt is about 4.6 mg/mL of the ephedrine hydrochloride.

EXAMPLES

Aspects of embodiments may be further understood in light of the following examples, which should not be construed as limiting in any way.

Example 1. Ready-to-Use Ephedrine Sulfate Composition

A ready-to-use injectable composition of ephedrine sulfate was prepared at 50 L scale by combining ephedrine sulfate USP/EP powder (Lot #18130597, Siegfried Pharma-Chemikalien, Minden Germany), sodium chloride USP/EP (Lot #18804697, Merck & Co., Kenilworth, N.J.), and water for injection in the amounts shown in Table 1, below, in a 200 L stainless steel vessel.

TABLE 1

| Component | Compendial Designation | Amount per 10 cc vial |
|---|---|---|
| Ephedrine sulfate | USP/EP | 50 mg |
| Sodium chloride | USP/EP | 90 mg |
| Water for injection | USP/EP | q.s. to 10 mL |

Two 20 mL vials of the mixed solution were sampled at this stage, and indicated that ephedrine sulfate was present in the solution at 100.2%-102.2% of the desired 5 mg/mL amount. A bioburden test of 200 mL of the mixed solution at this stage also revealed an acceptable level of biological components (0-0.1 CFU/mL).

After mixing, the solution was filtered through Opticap® XL4 Durapore® non-fiber releasing membrane filter membranes (lot #18131597, Merck Millipore, Burlington, Mass.) before filling 10 cc clear glass type I vials (Lot #18500797, Gerres-heimer/Bormioli, Düsseldorf, Germany) that had been washed and depyrogenized. The vials were capped with chlorobutyl FluroTec® ethylene tetrafluoroethylene (ETFE) fluoropolymer film coated stoppers (lot #18803297, West Pharma, Exton, Pa.), and flip-off caps (lot #18700897, Capsulit S.p.A., Roncello, Italy).

The pH level of the solution in the vials ranged from 5.6-6.2, well within the acceptable range of 4.5-7.0. Ephedrine sulfate was present in the solution in the vials in amounts ranging from 100.8% to 102.5% of the desired 5 mg/mL concentration. Bioburden testing of the solution in the vials revealed 0 CFU/mL.

The capped vials were crimped and sterilized by the overkill approach at 122.1° C. for 15 minutes in steel cassettes in an A601A autoclave.

Visual inspection of the terminally sterilized vials revealed no extraneous matter, low product volume or cosmetic defects. The sterilized vials passed sterility testing consistent with USP method <71> and passed bacterial endotoxins testing by USP method <87> (≤1.7 Eu/mg).

Bioburden testing on twenty pooled stoppers after filling indicated a range of 0-0.5 CFU/mL.

Analysis of three lots of ready-to-use 10-mL vials of ephedrine sulfate prepared by this method is shown Table 2, below:

TABLE 2

| Analysis | Lot 1 | Lot 2 | Lot 3 |
|---|---|---|---|
| Appearance | Clear, colorless, no visible particulate matter | | |
| Identification by UV | UV spectrum conforms to USP Reference Standard | | |
| Identification by HPLC | Retention time of ephedrine peak corresponds to USP Reference Standard | | |
| Volume in Container | 10.6 mL | 10.7 mL | 10.6 mL |
| Osmolality | 316 mOsm/kg | 314 mOsm/kg | 319 mOsm/kg |
| pH | 5.8 | 5.5 | 5.8 |
| (−)-Ephedrine | 101.1% of label claim | 101.0% of label claim | 101.4% of label claim |
| (+)-Ephedrine | ND* | ND | ND |
| Individual Unknown Impurities | <LOQ** | <LOQ | <LOQ |
| Total Impurities | <LOQ | <LOQ | <LOQ |
| Particulate Matter | ≥10 µm: 9 per container; ≥25 µm: 2 per container | ≥10 µm: 19 per container; ≥25 µm: 5 per container | ≥10 µm: 41 per container; ≥25 µm: 11 per container |
| Sterility (USP <71>) | Pass | Pass | Pass |
| Bacterial Endotoxins (USP <87>) | Pass | Pass | Pass |

*ND = None Detected.
**LOQ = Level of Quantification.

Example 2. Real-Time Stability of Ready-to-Use Ephedrine Sulfate Compositions 10-mL batches of ephedrine sulfate injection, 5 mg/mL, were prepared in each of 510 10-mL Type I flint glass vials (Gerresheimer/Bormioli), closed with 20 mm chlorobutyl flurotec-coated stoppers (West) and sealed with a 20 mm flip-off aluminum crimp seal (Capsult) in a production facility using standard production equipment, processes, personnel and procedures, all consistent with the method disclosed in Example 1. Ephedrine sulfate API was sourced from Siegfried PharmaChemikalien Minden GmbH (Germany).

The vials were stored at 25+/−2° C. and 60+/−5% relative humidity (RH) for 24 months in a controlled access, secure cabinet or security chamber and only withdrawn for testing.

Some vials were stored upright, while others were stored inverted (e.g., liquid in contact with the vial closures). Samples were identified and records were kept in a stability study log.

Vials were tested according to the parameters shown in Table 3, at the time points shown in Table 4, and by upright/inverted vial designation as shown in Table 5, below:

TABLE 3

| Test | Specification | Test Method | Vial Counts |
|---|---|---|---|
| Visual Inspection:<br>A) Physical appearance<br>B) Clarity<br>C) Particulate matter<br>D) Visual color | A) 10 cc flint glass vial sealed with a stopper and aluminum seal<br>B) Clear<br>C) No visible particulates<br>D) Colorless | QC-021 | Use assay vials |
| pH | 4.5 to 7.0 | USP <791> | 2 |
| Particulate matter (HIAC) | For particles ≥10 µm: NMT 6000 per container;<br>For particles ≥25 µm: NMT 600 per container | USP <788> | 10 |
| Osmolality | 270-330 mOsm/kg | QC-028 | 2 |
| Ephedrine sulfate assay (5 mg/mL) | 95.0-105.0% of label claim | EPH-001 | 3 |
| Enantiomeric purity (Chiral HPLC) | NMT 0.5% (+)-1S,2R-Ephedrine | EPH-003 | 2 |
| Related substances | ≤0.2% Unknown individual impurity;<br>≤0.75% Total impurities | EPH-001 | Use assay vials |
| Sterility | Sterile | USP <71> | 20 |
| Bacterial endotoxins | NMT 7.0 EU/mg | USP <85> | 3 |

TABLE 4

| Data point | Timing |
|---|---|
| Time Zero | Date on which samples were placed into the stability chamber |
| 3 Months | Pull date for analysis occurs +/− 1 week of the 3-month anniversary date of Time Zero |
| 6 Months | Pull date for analysis occurs +/− 1 week of the 6-month anniversary date of Time Zero |
| 9 Months | Pull date for analysis occurs +/− 1 week of the 9-month anniversary date of Time Zero |
| 12 Months | Pull date for analysis occurs +/− 2 weeks of the 12-month anniversary date of Time Zero |
| 18 Months | Pull date for analysis occurs +/− 2 weeks of the 18-month anniversary date of Time Zero |
| 24 Months | Pull date for analysis occurs +/− 4 weeks of the 24-month anniversary date of Time Zero |

TABLE 5

| Test | Time Point (months) | | | | | | |
|---|---|---|---|---|---|---|---|
| | 0 | 3 | 6 | 9 | 12 | 18 | 24 |
| Visual Inspection:<br>A) Physical appearance<br>B) Clarity<br>C) Particulate matter<br>D) Visual color | U | UI | UI | UI | UI | UI | UI |
| pH | U | UI | UI | UI | UI | UI | UI |
| Particulate matter (HIAC) | U | UI | UI | UI | UI | UI | UI |
| Osmolality | U | NP | NP | NP | UI | NP | UI |
| Ephedrine sulfate assay (5 mg/mL) | U | UI | UI | UI | UI | UI | UI |
| Enantiomeric purity (Chiral HPLC) | U | UI | UI | UI | UI | UI | UI |
| Related substances | U | UI | UI | UI | UI | UI | UI |
| Sterility | U | NP | NP | NP | I | NP | NP |
| Bacterial endotoxins | U | NP | NP | NP | NP | NP | I |
| Elemental Impurities | NP | NP | NP | NP | I | NP | I |
| Container/Closure Integrity Testing (CCIT) | UI | NP | NP | NP | NP | NP | I |

U: Upright orientation;
I: Inverted orientation;
NP: Not performed

The number of vials pulled for testing at each time point is summarized in Table 6 below:

TABLE 6

| Test | Time Point (months) | | | | | | |
|---|---|---|---|---|---|---|---|
| | 0 | 3 | 6 | 9 | 12 | 18 | 24 |
| Upright | 46 | 17 | 17 | 17 | 19 | 17 | 19 |
| Inverted | NP | 17 | 17 | 17 | 39 | 17 | 42 |

NP: Not performed

Quantitative analyses were plotted as mean values as a function of time, while qualitative analyses were recorded and summarized so that profile changes could be reviewed and conclusions drawn.

Results of Real-Time Stability Study

1. Physical Appearance

Specification:
A) 10 cc flint glass vial seal with a stopper and aluminum seal
B) Clear
C) No visible particulates
D) Colorless

TABLE 7

Physical Appearance Results

| | | Stability Time Point | | | | | | | | | | | |
|---|---|---|---|---|---|---|---|---|---|---|---|---|---|
| | | 3 months | | 6 months | | 9 months | | 12 months | | 18 months | | 24 months | |
| Lot | Initial | Up | Inv | Up | Inv | Up | Inv | Up | Inv | Up | Inv | Up | Inv |
| 1 | MR | MR | MR | MR | MR | MR | MR | MR | MR | MR | MR | MR | MR |
| 2 | MR | MR | MR | MR | MR | MR | MR | MR | MR | MR | MR | MR | MR |
| 3 | MR | MR | MR | MR | MR | MR | MR | MR | MR | MR | MR | MR | MR |

MR = Meets Requirements

2. Osmolality
Specification: 270-330 mOsm/kg

TABLE 8

Osmolality Results

| | | \_\_3 months\_\_ | | \_\_6 months\_\_ | | \_\_9 months\_\_ | | \_\_12 months\_\_ | | \_\_18 months\_\_ | | \_\_24 months\_\_ | |
|---|---|---|---|---|---|---|---|---|---|---|---|---|---|
| Lot | Initial | Up | Inv | Up | Inv | Up | Inv | Up | Inv | Up | Inv | Up | Inv |
| 1 | 316 | NP | NP | NP | NP | NP | NP | 320 | 319 | NP | NP | 327 | 323 |
| 2 | 314 | NP | NP | NP | NP | NP | NP | 317 | 316 | NP | NP | 318 | 317 |
| 3 | 319 | NP | NP | NP | NP | NP | NP | 318 | 317 | NP | NP | 319 | 318 |

NP = Not Performed 3. pH
Specification: Between 4.5 and 7.0

TABLE 9 pH Results

| | | \_\_3 months\_\_ | | \_\_6 months\_\_ | | \_\_9 months\_\_ | | \_\_12 months\_\_ | | \_\_18 months\_\_ | | \_\_24 months\_\_ | |
|---|---|---|---|---|---|---|---|---|---|---|---|---|---|
| Lot | Initial | Up | Inv | Up | Inv | Up | Inv | Up | Inv | Up | Inv | Up | Inv |
| 1 | 5.8 | 6.1 | 5.9 | 5.4 | 5.5 | 5.9 | 5.8 | 6.7 | 6.2 | 5.7 | 5.7 | 5.7 | 5.6 |
| 2 | 5.5 | 5.8 | 5.8 | 5.7 | 5.6 | 5.7 | 5.7 | 6.5 | 6.6 | 5.8 | 5.7 | 5.6 | 5.6 |
| 3 | 5.8 | 5.9 | 6.2 | 6.0 | 5.9 | 5.8 | 5.9 | 6.5 | 6.6 | 5.8 | 5.8 | 5.7 | 5.7 |

4. Ephedrine Sulfate Assay (5 mg/mL)
Specification: 95.0%-105.0% of label claim

TABLE 10

Ephedrine Sulfate Assay Results

| | | \_\_3 months\_\_ | | \_\_6 months\_\_ | | \_\_9 months\_\_ | | \_\_12 months\_\_ | | \_\_18 months\_\_ | | \_\_24 months\_\_ | |
|---|---|---|---|---|---|---|---|---|---|---|---|---|---|
| Lot | Initial | Up | Inv | Up | Inv | Up | Inv | Up | Inv | Up | Inv | Up | Inv |
| 1 | 101.1% | 101.0 | 100.9 | 100.9 | 101.1 | 101.5 | 101.3 | 100.7 | 100.7 | 101.0 | 101.2 | 102.2 | 101.6 |
| 2 | 101.0% | 100.4 | 100.4 | 100.3 | 100.8 | 100.8 | 102.0 | 100.1 | 100.0 | 100.8 | 101.1 | 101.5 | 101.0 |
| 3 | 101.4% | 100.7 | 100.4 | 100.6 | 100.9 | 101.8 | 101.0 | 99.4 | 99.2 | 101.0 | 100.5 | 101.1 | 101.2 |

5. Enantiomeric Purity
Specification: (+)-1S,2R-Ephedrine, NMT 0.5% by chiral HPLC

TABLE 11

Enantiomeric Purity Results

| | | \_\_3 months\_\_ | | \_\_6 months\_\_ | | \_\_9 months\_\_ | | \_\_12 months\_\_ | | \_\_18 months\_\_ | | \_\_24 months\_\_ | |
|---|---|---|---|---|---|---|---|---|---|---|---|---|---|
| Lot | Initial | Up | Inv | Up | Inv | Up | Inv | Up | Inv | Up | Inv | Up | Inv |
| 1 | ND | <LOQ | <LOQ | ND | ND | ND | ND | ND | ND | ND | ND | ND | ND |
| 2 | ND | <LOQ | <LOQ | ND | ND | ND | ND | ND | ND | ND | ND | ND | ND |
| 3 | ND | <LOQ | <LOQ | ND | ND | ND | ND | ND | ND | ND | ND | ND | ND |

ND = None Detected; LOQ = Limit of Quantitation

6. Related Substance: Any Unknown Individual Impurity
Specification: Any unknown individual impurity, 0.2% by HPLC

TABLE 12A

Related Substances Results: Any unknown individual impurity

| Lot | Initial | Stability Time Point | | | | | | | | | | | |
|---|---|---|---|---|---|---|---|---|---|---|---|---|---|
| | | 3 months | | 6 months | | 9 months | | 12 months | | 18 months | | 24 months | |
| | | Up | Inv | Up | Inv | Up | Inv | Up | Inv | Up | Inv | Up | Inv |
| 1 | <LOQ | <LOD | <LOQ | ND | <LOQ | 0.0 | 0.0 | <LOQ | <LOQ | <LOQ | <LOQ | <LOQ | 0.2% |
| 2 | <LOQ | <LOQ | <LOD | <LOQ | <LOQ | 0.0 | 0.0 | <LOQ | <LOQ | <LOQ | <LOQ | 0.1% | 0.1% |
| 3 | <LOQ | <LOQ | <LOQ | <LOQ | ND | 0.0 | 0.0 | <LOQ | <LOQ | <LOQ | <LOQ | 0.1% | <LOQ |

LOQ = Limit of Quantitation;
LOD = Limit of Detection;
ND = None Detected

7. Related Substance: Total Impurities
Specification:
  Total impurities, 0.75% by HPLC

TABLE 12B

Related Substances Results: Total impurities

| Lot | Initial | Stability Time Point | | | | | | | | | | | |
|---|---|---|---|---|---|---|---|---|---|---|---|---|---|
| | | 3 months | | 6 months | | 9 months | | 12 months | | 18 months | | 24 months | |
| | | Up | Inv | Up | Inv | Up | Inv | Up | Inv | Up | Inv | Up | Inv |
| 1 | <LOQ | <LOD | <LOQ | ND | <LOQ | 0.02 | 0.02 | <LOQ | <LOQ | <LOQ | <LOQ | <LOQ | 0.19% |
| 2 | <LOQ | <LOQ | <LOD | <LOQ | <LOQ | 0.02 | 0.02 | <LOQ | <LOQ | <LOQ | <LOQ | 0.09% | 0.09% |
| 3 | <LOQ | <LOQ | <LOQ | <LOQ | ND | 0.02 | 0.01 | <LOQ | <LOQ | <LOQ | <LOQ | 0.11% | <LOQ |

LOQ = Limit of Quantitation;
LOD = Limit of Detection;
ND = None Detected

8. Particulate Matter
Specification:
  A) For particles ≥10 μm, NMT 6000 per container by HIAC
  B) For particles ≥25 μm, NMT 600 per container by HIAC

TABLE 13

Particulate Matter Results

| Lot | Initial | Stability Time Point | | | | | | | | | | | |
|---|---|---|---|---|---|---|---|---|---|---|---|---|---|
| | | 3 months | | 6 months | | 9 months | | 12 months | | 18 months | | 24 months | |
| | | Up | Inv | Up | Inv | Up | Inv | Up | Inv | Up | Inv | Up | Inv |
| 1 | A) 9 | A) 94 | A) 167 | A) 1113 | A) 363 | A) 133 | A) 94 | A) 149 | A) 199 | A) 73 | A) 59 | A) 174 | A) 139 |
| | B) 2 | B) 0 | B) 0 | B) 1 | B) 0 | B) 1 | B) 0 | B) 1 | B) 0 | B) 0 | B) 0 | B) 1 | B) 0 |
| 2 | A) 19 | A) 96 | A) 63 | A) 717 | A) 273 | A) 215 | A) 189 | A) 83 | A) 134 | A) 45 | A) 124 | A) 254 | A) 518 |
| | B) 5 | B) 0 | B) 0 | B) 1 | B) 0 | B) 0 | B) 1 | B) 0 | B) 1 | B) 0 | B) 1 | B) 0 | B) 0 |
| 3 | A) 41 | A) 315 | A) 45 | A) 673 | A) 354 | A) 209 | A) 237 | A) 173 | A) 97 | A) 201 | A) 85 | A) 145 | A) 121 |
| | B) 11 | B) 0 | B) 0 | B) 4 | B) 1 | B) 0 | B) 0 | B) 0 | B) 0 | B) 0 | B) 1 | B) 0 | B) 1 |

9. Sterility
Specification: Sterile

TABLE 14

Sterility Results

| | | \multicolumn{12}{c|}{Stability Time Point} |
| | | 3 months | | 6 months | | 9 months | | 12 months | | 18 months | | 24 months | |
| Lot | Initial | Up | Inv | Up | Inv | Up | Inv | Up | Inv | Up | Inv | Up | Inv |
|---|---|---|---|---|---|---|---|---|---|---|---|---|---|
| 1 | Sterile | NP | NP | NP | NP | NP | NP | NP | Sterile | NP | NP | NP | NP |
| 2 | Sterile | NP | NP | NP | NP | NP | NP | NP | Sterile | NP | NP | NP | NP |
| 3 | Sterile | NP | NP | NP | NP | NP | NP | NP | Sterile | NP | NP | NP | NP |

NP = Not Performed

10. Bacterial Endotoxins
Specification: NMT 7.0 EU/mg

TABLE 15

Bacterial Endotoxins Results

| | | \multicolumn{12}{c|}{Stability Time Point} |
| | | 3 months | | 6 months | | 9 months | | 12 months | | 18 months | | 24 months | |
| Lot | Initial | Up | Inv | Up | Inv | Up | Inv | Up | Inv | Up | Inv | Up | Inv |
|---|---|---|---|---|---|---|---|---|---|---|---|---|---|
| 1 | MR | NP | NP | NP | NP | NP | NP | NP | NP | NP | NP | NP | <0.2 |
| 2 | MR | NP | NP | NP | NP | NP | NP | NP | NP | NP | NP | NP | <0.2 |
| 3 | MR | NP | NP | NP | NP | NP | NP | NP | NP | NP | NP | NP | <0.2 |

MR = Meets Requirements;
NP = Not Performed

11. Elemental Impurities
Specification: Meets the requirements of USP <232>

TABLE 16

Elemental Impurities Results

| | | \multicolumn{12}{c|}{Stability Time Point} |
| | | 3 months | | 6 months | | 9 months | | 12 months | | 18 months | | 24 months | |
| Lot | Initial | Up | Inv | Up | Inv | Up | Inv | Up | Inv | Up | Inv | Up | Inv |
|---|---|---|---|---|---|---|---|---|---|---|---|---|---|
| 1 | NP | NP | NP | NP | NP | NP | NP | NP | MR | NP | NP | NP | MR |
| 2 | NP | NP | NP | NP | NP | NP | NP | NP | MR | NP | NP | NP | MR |
| 3 | NP | NP | NP | NP | NP | NP | NP | NP | MR | NP | NP | NP | MR |

MR = Meets Requirements;
NP = Not Performed

12. Container/Closure Integrity Testing (CCIT)
Specification: Integral

TABLE 17

CCIT Results

| | | \multicolumn{12}{c|}{Stability Time Point} |
| | | 3 months | | 6 months | | 9 months | | 12 months | | 18 months | | 24 months | |
| Lot | Initial | Up | Inv | Up | Inv | Up | Inv | Up | Inv | Up | Inv | Up | Inv |
|---|---|---|---|---|---|---|---|---|---|---|---|---|---|
| 1 | MR | NP | NP | NP | NP | NP | NP | NP | NP | NP | NP | NP | MR |
| 2 | MR | NP | NP | NP | NP | NP | NP | NP | NP | NP | NP | NP | MR |
| 3 | MR | NP | NP | NP | NP | NP | NP | NP | NP | NP | NP | NP | MR |

MR = Meets Requirements;
NP = Not Performed

Example 3. Accelerated Stability Study of Ready-to-Use Ephedrine Sulfate Compositions 10-mL batches of ephedrine sulfate injection, 5 mg/mL, were prepared in each of 510 10-mL Type I flint glass vials (Gerresheimer/Bormioli), closed with 20 mm chlorobutyl flurotec-coated stoppers (West) and sealed with a 20 mm flip-off aluminum crimp seal (Capsult) in a production facility using standard production equipment, processes, personnel and procedures, all consistent with the method disclosed in Example 1. Ephedrine sulfate API was sourced from Siegfried PharmaChemikalien Minden GmbH (Germany).

The vials were stored at 40+/−2° C. and 75+/−5% relative humidity (RH) for 6 months in a controlled access, secure stability chamber and only withdrawn for testing. Some vials were stored upright, while others were stored inverted (e.g., liquid in contact with the vial closures). Samples were identified and records were kept in a stability study log.

Vials were tested according to the parameters shown in Table 18, at the time points shown in Table 19, and by upright/inverted vial designation as shown in Table 20, below:

TABLE 18

| Test | Specification | Test Method | Vial Counts |
| --- | --- | --- | --- |
| Visual Inspection:<br>A) Physical appearance<br>B) Clarity<br>C) Particulate matter<br>D) Visual color | A) 10 cc flint glass vial sealed with a stopper and aluminum seal<br>B) Clear<br>C) No visible particulates<br>D) Colorless | QC-021 | Use assay vials |
| pH | 4.5 to 7.0 | USP <791> | 2 |
| Particulate matter (HIAC) | For particles ≥10 μm: NMT 6000 per container;<br>For particles ≥25 μm: NMT 600 per container | USP <788> | 10 |
| Osmolality | 270-330 mOsm/kg | QC-028 | 2 |
| Ephedrine sulfate assay (5 mg/mL) | 95.0-105.0% of label claim | EPH-001 | 3 |
| Enantiomeric purity (Chiral HPLC) | NMT 1.0% (+)-1S,2R-Ephedrine | EPH-003 | 2 |
| Related substances | ≤0.2% Unknown individual impurity;<br>≤0.75% Total impurities | EPH-001 | Use assay vials |
| Sterility | Sterile | USP <71> | 20 |
| Bacterial endotoxins | NMT 7.0 EU/mg | USP <85> | 3 |

TABLE 19

| Data point | Timing |
| --- | --- |
| Time Zero | Date on which samples were placed into the stability chamber |
| 1 Month | Pull date for analysis occurs +/− 1 week of the 1-month anniversary date of Time Zero |
| 3 Months | Pull date for analysis occurs +/− 1 week of the 3-month anniversary date of Time Zero |
| 6 Months | Pull date for analysis occurs +/− 1 week of the 6-month anniversary date of Time Zero |

TABLE 20

| | Time Point (months) | | | |
| --- | --- | --- | --- | --- |
| Test | 0 | 1 | 3 | 6 |
| Visual Inspection:<br>A) Physical appearance<br>B) Clarity<br>C) Particulate matter<br>D) Visual color | UI | UI | UI | UI |
| pH | UI | UI | UI | UI |
| Particulate matter (HIAC) | UI | UI | UI | UI |
| Osmolality | NP | NP | NP | UI |
| Ephedrine sulfate assay (5 mg/mL) | UI | UI | UI | UI |
| Enantiomeric purity (Chiral HPLC) | U | UI | UI | UI |
| Related substances | U | UI | UI | UI |

U: Upright orientation;
I: Inverted orientation;
NP: Not performed

The number of vials pulled for testing at each time point is summarized in Table 21 below:

TABLE 21

| | Time Point (months) | | | |
| --- | --- | --- | --- | --- |
| Test | 0 | 1 | 3 | 6 |
| Upright | NP | 17 | 17 | 19 |
| Inverted | NP | 17 | 17 | 19 |

NP: Not performed

Quantitative analyses were plotted as mean values as a function of time, while qualitative analyses were recorded and summarized so that profile changes can be reviewed and conclusions drawn.

Results of Accelerated Stability Study

1. Physical Appearance

Specification:

A) 10 cc flint glass vial seal with a stopper and aluminum seal

B) Clear

C) No visible particulates

D) Colorless

TABLE 22

| Physical Appearance Results | | | | | | |
| --- | --- | --- | --- | --- | --- | --- |
| | Stability Time Point | | | | | |
| | 1 month | | 3 months | | 6 months | |
| Lot | Up | Inv | Up | Inv | Up | Inv |
| 1 | MR | MR | MR | MR | MR | MR |
| 2 | MR | MR | MR | MR | MR | MR |
| 3 | MR | MR | MR | MR | MR | MR |

MR = Meets Requirements

2. Osmolality

Specification: 270-330 mOsm/kg

TABLE 23

Osmolality Results

| | Stability Time Point | | | | | |
|---|---|---|---|---|---|---|
| | 1 month | | 3 months | | 6 months | |
| Lot | Up | Inv | Up | Inv | Up | Inv |
| 1 | NP | NP | NP | NP | 318 | 320 |
| 2 | NP | NP | NP | NP | 315 | 314 |
| 3 | NP | NP | NP | NP | 318 | 314 |

NP = Not Performed 3. pH

Specification: Between 4.5 and 7.0

TABLE 24 pH Results

| | Stability Time Point | | | | | |
|---|---|---|---|---|---|---|
| | 1 month | | 3 months | | 6 months | |
| Lot | Up | Inv | Up | Inv | Up | Inv |
| 1 | 5.6 | 5.7 | 5.8 | 5.6 | 6.0 | 6.1 |
| 2 | 5.7 | 5.7 | 5.8 | 5.8 | 6.2 | 5.8 |
| 3 | 5.9 | 5.8 | 5.9 | 5.8 | 5.8 | 5.9 |

4. Ephedrine Sulfate Assay (5 mg/mL)

Specification: 95.0%-105.0% of label claim

TABLE 25

Ephedrine Sulfate Assay Results

| | Stability Time Point | | | | | |
|---|---|---|---|---|---|---|
| | 1 month | | 3 months | | 6 months | |
| Lot | Up | Inv | Up | Inv | Up | Inv |
| 1 | 101.5% | 101.6% | 101.3% | 100.9% | 100.8% | 100.9% |
| 2 | 100.8% | 100.3% | 100.7% | 100.3% | 100.7% | 99.9% |
| 3 | 100.8% | 100.7% | 100.4% | 100.6% | 100.6% | 100.1% |

5. Enantiomeric Purity

Specification: (+)-1S,2R-Ephedrine, NMT 0.5% by chiral HPLC

TABLE 26

Enantiomeric Purity Results

| | Stability Time Point | | | | | |
|---|---|---|---|---|---|---|
| | 1 month | | 3 months | | 6 months | |
| Lot | Up | Inv | Up | Inv | Up | Inv |
| 1 | ND | ND | <LOQ | <LOQ | ND | ND |
| 2 | ND | ND | <LOQ | <LOQ | ND | ND |
| 3 | ND | ND | <LOD | <LOQ | ND | ND |

ND = None Detected;
LOQ = Limit of Quantitation

6. Related Substance

Specification:
A) Unknown individual impurities, 0.2%
B) Total impurities, ≤0.75%

TABLE 27

Related Substances Results

| | Stability Time Point | | | | | |
|---|---|---|---|---|---|---|
| | 1 month | | 3 months | | 6 months | |
| Lot | Up | Inv | Up | Inv | Up | Inv |
| 1 | A) <LOQ | A) <LOQ | A) <LOD | A) <LOQ | A) ND | A) <LOQ |
| | B) <LOQ | B) <LOQ | B) <LOD | B) <LOQ | B) ND | B) <LOQ |
| 2 | A) <LOQ | A) <LOQ | A) <LOQ | A) <LOQ | A) <LOQ | A) <LOQ |
| | B) <LOQ | B) <LOQ | B) <LOQ | B) <LOQ | B) <LOQ | B) <LOQ |
| 3 | A) <LOQ | A) <LOQ | A) <LOQ | A) <LOD | A) <LOQ | A) ND |
| | B) <LOQ | B) <LOQ | B) <LOQ | B) <LOD | B) <LOQ | B) ND |

LOQ = Limit of Quantitation;
LOD = Limit of Detection;
ND = None Detected

7. Particulate Matter

Specification:
A) For particles 10 μm, NMT 6000 per container by HIAC
B) For particles 25 μm, NMT 600 per container by HIAC

TABLE 28

Particulate Matter Results

| | Stability Time Point | | | | | |
|---|---|---|---|---|---|---|
| | 1 month | | 3 months | | 6 months | |
| Lot | Up | Inv | Up | Inv | Up | Inv |
| 1 | A) 455 | A) 290 | A) 104 | A) 128 | A) 120 | A) 363 |
| | B) 1 | B) 1 | B) 0 | B) 0 | B) 0 | B) 0 |
| 2 | A) 139 | A) 389 | A) 6 | A) 155 | A) 271 | A) 90 |
| | B) 1 | B) 1 | B) 5 | B) 0 | B) 1 | B) 1 |
| 3 | A) 1087 | A) 552 | A) 101 | A) 101 | A) 196 | A) 120 |
| | B) 5 | B) 0 | B) 0 | B) 1 | B) 1 | B) 0 |

Example 4. Extractable and Leachable Substances Study

Ephedrine Sulfate in 0.9% Sodium Chloride Injection, 50 mg/10 mL, (5 mg/mL) was packaged in a 10 cc Type I glass vial with a Flurotec coated Chlorobutyl rubber stopper (20 mm 4110/40, Grey, B2-40 from West). This Extractable and Leachable (E&L) study was designed based on the guidelines provided in USP <1663>, <1664>.

Whole stoppers were immersed and refluxed (exposing the uncoated surface as well) in extraction solvents offering greater extracting power than ready-to-use ephedrine compositions consistent with the present disclosure overnight for a minimum of 12 hours in three solvents: water pH 3.4, water pH 9.4 and IPA/Water (50/50). Additionally, a leachables analysis was performed by QTOF GC-MS, QTOF LC-MS and HPLC for three exhibit batches of ready-to-use ephedrine sulfate composition samples of Example 2 that were stored in an inverted orientation for 24 months at 25° C.±2° C. and 60%±5% relative humidity (RH). In order to extract metal impurities, an extractable study was performed on stoppers and vials using 2% HNO₃ and the extracts were screened using ICP-MS analysis. Additionally, three exhibit batches of ready-to-use ephedrine sulfate composition samples of Example 2 that were stored in an inverted position for 24 months at 25° C.±2° C. and 60%±5% RH were analyzed for Class 1 and 2A elements.

Summary Results.

The extracts from the extractable study performed on stoppers were analyzed by GC-MS for volatile and semi-volatile compounds and by LC-MS for non-volatile compounds. The control samples were also prepared and analyzed along with all exposed extractable samples and the drug product stability samples. The MS study was performed by an independent laboratory using LC-MS and GC-MS to identify and relatively quantify the extractables and leachables in the extracts or in the ready-to-use ephedrine sulfate compositions. Subsequently, a leachable study was also performed by a High-Pressure Liquid Chromatography (HPLC) based validated method (EPH-006).

Most of the identified extractables appeared to be originating from the uncoated surface of the stoppers. Extractables included siloxane oligomers, non-ionic surfactants (Laureth-9 and related), sulfur compounds, Butylated hydroxytoluene (BHT) and fatty acids (mineral fillers) commonly used in the production of elastomeric components. Another extractable found in the LC-MS analysis was Triethylene glycol which is a common plasticizer used in the production of vinyl polymers. During the leachable analysis, a compound consistent with bis(2-ethylhexyl) isophthalate was detected in the ready-to-use ephedrine sulfate composition samples at a concentration of 0.15 µg/mL or lower by QTOF-GCMS. Another compound consistent with dichlorobenzoic acid (DCBA) was also detected in the ready-to-use ephedrine sulfate composition samples at levels of 1.4 µg/mL or lower by QTOF-LCMS-UV-CAD. Dichlorobenzoic acid was also detected during the HPLC analysis using test method EPH-006 at the concentration of 0.7 µg/mL or lower. It is to be noted that DCBA detected both by the MS study and the HPLC analysis was also detected previously during the leachable analysis of the 18-month samples of the ready-to-use ephedrine sulfate compositions.

Based on MS study and HPLC analysis, the maximum amount of dichlorobenzoic acid (DCBA found was ~1.4 ppm (~0.02% with respect to Ephedrine Sulfate) in one sample of ready-to-use ephedrine sulfate composition stored in the inverted position for 24 months. As per ICH guidelines (Impurities in New drug products Q3B R2) the identification threshold for any impurities that may be present in Ephedrine Sulfate is 0.2% and the qualification threshold is 0.5%. The amount of DCBA found in this inverted stored sample was below the limit of quantitation (LOQ) i.e. <0.1 ppm.

For the evaluation of elemental impurities, the extracts from the stoppers and vials were analyzed by ICP-MS. Results obtained from the ICPMS analysis of the extracting solutions indicates that the Class 1, 2A and 3 were found to be below the respective established PDEs. Furthermore, three exhibit batches of ready-to-use ephedrine sulfate compositions of Example 2 stored in an inverted position for 24 months at 25° C.±2° C. and 60%±5% RH were analyzed for Class 1 and 2A elements by ICP-MS. All tested elemental impurities were found to be significantly lower their established permitted daily exposure (PDE) values. Therefore, based on the data from this extractable and leachable study, the safety risk associated with leachables or metallic impurities in the ready-to-use ephedrine sulfate compositions consistent with the present disclosure appears to be low.

Extractables Study

Stoppers were extracted using three extraction solvents mentioned below. a) Water adjusted to pH 3.4 using 1N HCl b) Water adjusted to pH 9.4 using 1N NaOH c) IPA/Water 50%/50% (v/v) Three sets of 10 stoppers (weight~16.8 g each) were transferred into three separate 250 mL round bottom flasks. 100 mL each of pH 3.4 aqueous solution, pH 9.4 aqueous solution and IPA/Water (50:50 v/v) mixture were transferred into the three separate above-mentioned round bottom flasks. Each solvent containing 10 stoppers was refluxed to boiling overnight (minimum 12 hours). Reflux was performed for 12 hours each for the IPA/water mixture and the pH 3.4 solution and 20 hours for the pH 9.4 solution. Resulting solution from each reflux solvent was analyzed for extractables using QTOF LC-MS and GC-MS.

The extractable study intended to extract metals was performed on rubber stoppers and glass vials. 10 stoppers were weighed (weight ~17 g) and transferred into a 1 L plastic container. Approximately 200 mL (appropriate volume to immerse the stoppers) of 2% HNO₃ solution was transferred into the container having the stoppers and placed in an oven maintained at 60° C. for ~24 h. Similarly, 5 vials (weight ~20 g each) were transferred into a 1 L plastic container. Approximately 300 mL (appropriate volume to immerse vials) of 2% HNO₃ solution was transferred into the container having the vials and placed in an oven maintained at 60° C. for ~24 h. Additionally, the refluxed aqueous solution (pH 3.4 from the extractable study described above) was also analyzed for metal impurities as metals tend to be extracted more acidic solutions. Ten elements (Class 1, 2A and 3) were examined. Extracts were analyzed by ICP-MS based on USP <233> and following the ICH Q3D Permitted daily exposure (PDE) limits.

Extracts from each reflux solvent were analyzed for extractables using QTOF LC-MS and GC-MS. Extractables included siloxane oligomers, non-ionic surfactants (Laureth-9 and related), sulfur compounds, Butylated hydroxytoluene (BHT) and fatty acids (mineral fillers) commonly used in the production of elastomeric components. Another extractable found in the LC-MS analysis was Triethylene glycol which is a common plasticizer used in vinyl polymers.

Extractable compounds detected in the extracts along with relative quantitation are provided in Tables 29-32. According to the manufacturer, Bisphenol A (BPA), Melamine, 2-Mercaptobenzothiazole, Nitrosamines, Phthalates and Polyvinylchlorides (PVC) are not intentionally added to the stoppers.

TABLE 29

GCMS Extractables Results: 50/50 IPA/Water Extract

| RT (min) | Formula | Possible Identification | CAS | ID Source | Est. Conc. (μg/mL)* | Quantitation Standard |
|---|---|---|---|---|---|---|
| 5.808 | N/A | Siloxane-related (m/z 75, 77, 103, 117, 119, 161) | N/A | NIST | 0.58 | D5 |
| 6.802 | N/A | Siloxane-related (m/z 75, 77, 103, 117, 119, 161) | N/A | NIST | 0.16 | D5 |
| 8.677 | $C_8H_{24}O_4Si_4$ | Octamethyl cyclotetrasiloxane (D4) | 556-67-2 | NIST | 0.43 | D5 |
| 10.638 | $C_{10}H_{30}O_5Si_5$ | Decamethyl cyclopentasiloxane (D5) | 541-02-6 | NIST | 0.18 | D5 |
| 10.939 | N/A | Hydrocarbon** | N/A | NIST | 1.39 | Decane |
| 14.16 | $C_{15}H_{24}O$ | Butylated hydroxytoluene** | 128-37-0 | NIST | 1.30 | BHT |
| 14.216 | $S_6$ | Cyclohexasulfide | 13798-23-7 | NIST | 0.27 | Hexadecane |
| 14.454 | $C_{12}H_{24}O_2$ | Dodecanoic acid | 143-07-7 | NIST | 0.19 | Hexadecane |
| 15.686 | N/A | Hydrocarbon** | N/A | NIST | 4.46 | Hexadecane |
| 15.97 | $C_{14}H_{28}O_2$ | Tetradecanoic acid | 544-63-8 | NIST | 0.13 | Hexadecane |
| 17.396 | $C_{16}H_{32}O_2$ | Hexadecanoic acid | 57-10-3 | NIST | 2.59 | Eicosane |
| 18.217 | $S_8$ | Sulfur octamer | 10544-50-0 | NIST | 0.78 | Eicosane |
| 18.662 | $C_{18}H_{36}O_2$ | Stearic acid | 57-11-4 | NIST | 3.11 | Eicosane |

*Calculated from the average of duplicate injections based on the calibration equations:
Decane, $y = 6{,}247{,}104.5151x - 269{,}219.0219$, $R^2 = 0.9979$;
D5, $y = 16{,}686{,}845.9104x + 610{,}105.5710$, $R^2 = 0.9961$;
BHT, $y = 20{,}301{,}408.1745x - 86{,}101.7850$, $R^2 = 0.9967$;
Hexadecane, $y = 8{,}934{,}944.7600x + 59{,}660.8105$, $R^2 = 0.9924$;
Diisobutyl phthalate, $y = 14{,}576{,}196.4016x - 242{,}019.4874$, $R^2 = 0.9959$;
Eicosane, $y = 7{,}765{,}118.6556x - 109{,}508.8545$, $R^2 = 0.9923$.
**This compound was quantitated in the 5X diluted sample extract.

TABLE 30

HPLC-UV-CAD Extractables Results: pH 3.4 Extract

| RT (min) | Positive m/z | Negative m/z | Mass | Best Match | Possible Identification | Est. Conc. (μg/mL)* | Quantitation Standard |
|---|---|---|---|---|---|---|---|
| 1.232 | 151.0969 | | 150.0897 | $C_6H_{14}O_4$ | Triethylene glycol | <0.5 | 12-HDA |
| 1.321 | 166.1232 | | 165.1158 | $C_{10}H_{15}NO$ | Ephedrine** | 0.14 | Irgacure 184 |

*Calculated from the average of duplicate injections based on the calibration equations:
Irgacure 184 (UV), $y = 133.41x + 23.048$, $R^2 = 0.9917$;
12-HDA (12-Hydroxydodecanoic acid) (CAD), $y = 0.019x^2 - 0.0032x + 0.0866$, $R^2 = 1.0000$
**This compound is considered as a drug related compound, which is unique in the pH 3.4 extract compared to the pH 3.4 Control.

TABLE 31

HPLC-UV-CAD Extractables Results: pH 9.4 Extract

| RT (min) | Positive m/z | Negative m/z | Mass | Best Match | Possible Identification | Est. Conc. (μg/mL)* | Quantitation Standard |
|---|---|---|---|---|---|---|---|
| 1.232 | 151.0969 | | 150.0897 | $C_6H_{14}O_4$ | Triethylene glycol | <0.5 | 12-HDA |
| 1.746 | | 128.9321 | 129.9393 | $H_2O_4S_2$ | Dithionous acid | 3.52 | 12-HDA |
| 1.831 | | 143.9011 | 144.9086 | $HO_3S_3$ | Thionite related | | |
| 9.846 | 196.1335 | | 178.0998 | $C_{11}H_{14}O_2$ | 1-Hydroxy-1-phenyl-2-pentanone | 0.10 | Irgacure 184 |
| 18.072 | 440.4109 | | 439.4036 | $C_{27}H_{53}NO_3$ | Fatty amide related | <0.5 | Oleamide |

*Calculated from the average of duplicate injections based on the calibration equations:
Irgacure 184 (UV), $y = 133.41x + 23.048$, $R^2 = 0.9917$;
12-HDA (12-Hydroxydodecanoic acid) (CAD), $y = 0.019x^2 - 0.0032x + 0.0866$, $R^2 = 1.0000$;
Oleamide (CAD), $y = 0.0836x^2 - 0.4401x + 0.3694$, $R^2 = 1.0000$

TABLE 32

HPLC-UV-CAD Extractables Results: 50/50 IPA/Water Extract

| RT (min) | Positive m/z | Negative m/z | Mass | Best Match | Possible Identification | Est. Conc. (μg/mL)* | Quantitation Standard |
|---|---|---|---|---|---|---|---|
| 1.113 | 173.0788 | | 150.0895 | $C_6H_{14}O_4$ | Triethylene glycol | <0.5 | 12-HDA |
| 5.765 | 205.1438 | | 204.1365 | $C_{10}H_{20}O_4$ | Butyldiglycol acetate | <0.5 | 12-HDA |
| 6.883 | 223.0643 | | 222.0566 | $C_8H_{14}O_5S$ | Laureth sulfate related | <0.5 | 12-HDA |
| 6.887 | | 275.0362 | 240.0669 | $C_8H_{16}O_6S$ | Laureth sulfate related | <0.5 | 12-HDA |
| 7.012 | 343.2963 | | 342.289 | $C_{19}H_{38}N_2O_3$ | Lauramidopropyl betaine | <0.5 | 12-HDA |
| 10.905 | | 313.0784 | 268.0799 | $C_{10}H_{20}O_4S_2$ | 1,8,11,14-Tetraoxa-4,5-dithiacyclohexadecane | <0.5 | 12-HDA |
| 11.275 | N/A | N/A | N/A | N/A | UV Unknown | 0.41 | Irgacure 184 |
| 11.672 | N/A | N/A | N/A | N/A | UV Unknown | 0.22 | Irgacure 184 |
| 13.585 | 600.468 | | 582.4341 | $C_{30}H_{62}O_{10}$ | Laureth-9 | <0.5 | 12-HDA |
| 13.847 | | 199.1703 | 200.1776 | $C_{12}H_{24}O_2$ | Lauric acid | <0.5 | 12-HDA |
| 13.865 | 319.2845 | | 318.2804 | $C_{18}H_{38}O_4$ | Laureth-3 isomer | <0.5 | 12-HDA |
| 13.893 | 429.319 | | 406.3301 | $C_{22}H_{46}O_6$ | Laureth-5 isomer | <0.5 | 12-HDA |
| 13.958 | 385.2929 | | 362.3036 | $C_{20}H_{42}O_5$ | Laureth-4 isomer | <0.5 | 12-HDA |
| 14.618 | 614.4841 | | 596.4501 | $C_{31}H_{64}O_{10}$ | Laureth-9 related | <0.5 | 12-HDA |
| 14.965 | | 297.2432 | 298.2507 | $C_{18}H_{34}O_3$ | Ricinoleic acid | <0.5 | 12-HDA |
| 15.321 | 429.3191 | | 406.33 | $C_{22}H_{46}O_6$ | Laureth-5 | <0.5 | 12-HDA |
| 15.393 | 385.2931 | | 362.3039 | $C_{20}H_{42}O_5$ | Laureth-4 | <0.5 | 12-HDA |
| 15.427 | 319.2849 | | 318.2779 | $C_{18}H_{38}O_4$ | Laureth-3 | <0.5 | 12-HDA |
| 15.461 | 275.2586 | | 274.2513 | $C_{16}H_{34}O_3$ | Laureth-2 | <0.5 | 12-HDA |
| 15.913 | | 309.1739 | 264.174 | $C_{13}H_{28}O_3S$ | Dodecyl methanesulfonate | 0.65 | 12-HDA |
| 15.804 | 196.1333 | | 178.0995 | $C_{11}H_{14}O_2$ | 1-Hydroxy-1-phenyl-2-pentanone | 30.47 | Irgacure 184 |
| 15.924 | | 389.1612 | 390.1685 | $C_{22}H_{30}O_2S_2$ | 2,2'-Dithiobis[6-(1,1-dimethylethyl)-4-methylphenol] | | |
| 16.463 | | 255.233 | 256.2402 | $C_{16}H_{32}O_2$ | Palmitic acid | 10.74 | Oleamide |
| 16.563 | | 227.0749 | 228.0821 | $C_{11}H_{16}O_3S$ | 5-(tert-Butyl)-3-toluenesulfonic acid | 0.25 | Irgacure 184 |
| 16.845 | 306.2768 | | 283.2881 | $C_{18}H_{37}NO$ | Stearamide | <0.5 | Oleamide |
| 16.899 | | 227.2015 | 228.2088 | $C_{14}H_{28}O_2$ | Myristic acid | <0.5 | Oleamide |
| 16.928 | 256.2642 | | 255.2569 | $C_{16}H_{33}NO$ | Palmitamide | <0.5 | Oleamide |
| 17.107 | | 353.2001 | 354.2074 | $C_{16}H_{34}O_6S$ | Laureth-2 sulfate | <0.5 | Oleamide |
| 17.86 | 282.2799 | | 281.2726 | $C_{18}H_{35}NO$ | Oleamide | <0.5 | Oleamide |

*Calculated from the average of duplicate injections based on the calibration equations:
Irgacure 184 (UV), $y = 135.71x + 22.797$, $R^2 = 0.9913$;
12-HDA (12-Hydroxydodecanoic acid) (CAD), $y = 0.0219x^2 - 0.0041x + 0.1085$, $R^2 = 1.0000$;
Oleamide (CAD), $y = 0.0944x^2 - 0.526x + 0.5834$, $R^2 = 1.0000$ To evaluate the metal impurities, the 2% nitric acid stopper extracts and the pH 3.4 reflux extract were screened according to USP <233> based ICP-MS analysis and results are compared against established PDEs of the respective elements. Ten elements (Class 1, 2A and 3) were selected. Results obtained from the ICPMS analysis of the extracting solutions indicates that the Class 1, 2A and 3 elements were found to be below the respective established PDEs. ICP-MS results from the extractable study are summarized in Table 33.

TABLE 33

ICP-MS Results for Extractables Study

| Element | Class | Parenteral PDE (μg/day) | PDE limits calculated based on 10 mL daily max. injection volume (ppb)* | ICP-MS Results (ppb) Glass vials (2% $HNO_3$)** | ICP-MS Results (ppb) Stoppers (2% $HNO_3$)** | ICP-MS Results (ppb) Stoppers (Reflux pH 3.4)** |
|---|---|---|---|---|---|---|
| Cadmium | 1 | 2 | 200 | <2.5 | <2.5 | <2.5 |
| Lead | 1 | 5 | 500 | <2.5 | <2.5 | <2.5 |
| Arsenic | 1 | 15 | 1500 | <2.5 | <2.5 | <2.5 |
| Mercury | 1 | 3 | 300 | <2.5 | <2.5 | <2.5 |
| Cobalt | 2A | 5 | 500 | 2.6 | <2.5 | <2.5 |
| Vanadium | 2A | 10 | 1000 | <2.5 | <2.5 | 14.5 |
| Nickel | 2A | 20 | 2000 | <2.5 | <2.5 | 62.5 |

TABLE 33-continued

ICP-MS Results for Extractables Study

| Element | Class | Parenteral PDE (µg/day) | PDE limits calculated based on 10 mL daily max. injection volume (ppb)* | ICP-MS Results (ppb) Glass vials (2% HNO$_3$)** | ICP-MS Results (ppb) Stoppers (2% HNO$_3$)** | ICP-MS Results (ppb) Stoppers (Reflux pH 3.4)** |
|---|---|---|---|---|---|---|
| Lithium | 3 | 250 | 25000 | 2.6 | <2.5 | <2.5 |
| Antimony | 3 | 90 | 9000 | <2.5 | <2.5 | <2.5 |
| Copper | 3 | 300 | 30000 | 3.7 | <2.5 | <2.5 |

*PDE value in ppb = Parental PDE value (µg/day) ÷ maximum daily volume (mL/day), i.e., 10 mL/day * 1000.
**2.5 ppb corresponds to the lowest concentration of the respective element in the calibration curve.

Leachables Study

The three exhibit batches of ready-to-use ephedrine sulfate compositions of Example 2 stored in an inverted position for 24 months at 25° C.±2° C. and 60%±5% RH were subjected to a leachables study by QTOF GC-MS and LC-MS. A control sample was also prepared in a volumetric flask by dissolving 5 g of Ephedrine Sulfate API and 9 g of NaCl in 1 L purified water. The pH of the resulting solution was ~5.6.

In the MS study, identification and relative quantitation of leachables was achieved by GCMS QTOF and LC-MS QTOF analysis. The Analytical Evaluation Threshold (AET) was calculated to be 0.15 µg/mL based on the maximum daily dose of the proposed drug product and was set to 0.2 µg/mL in the GC-MS analysis and 0.1 µg/mL in the LC-MS analysis. The drug product samples from the three lots described in Example 2 were extracted as-is and at lower and higher pH to prepare the extracts for GC-MS analysis. The drug product samples were analyzed by LCMS analysis without further preparation. The summary of the leachable data for ephedrine sulfate injection samples is provided in Table 34, below. Reference Standards of varied structures and chromophores were employed in the MS study and quantitation of extractables and leachables were performed based on the calibration curve of closely matched reference standards.

MS/MS studies were also performed as required to aid identification from the fragmentation patterns. It is to be noted that the same test methods (GC-MS and LC-MS) were used for the identification and quantitation of extractables in the stopper extracts. The extensive list of extractables of varied structures detected by these methods demonstrate the versatility of these methods. It is evident from the MS data that numerous extractables were detected due to the rigorous conditions employed in the extractable study, however the only compounds detected during the leachable analysis were Dichlorobenzoic acid (1.4 µg/mL or lower) and trace amounts of Bis(2-ethylhexyl) isophthalate (0.15 µg/mL or lower). Results from the leachable identifications and the relative quantitation values are summarized below in Table 34.

TABLE 34

Leachables Identification and Relative Quantitation

| Formula | Possible Identification | Estimated Concentration in Sample (µg/mL) | | |
|---|---|---|---|---|
| | | Lot 1 | Lot 2 | Lot 3 |
| C$_{24}$H$_{38}$O$_4$ | 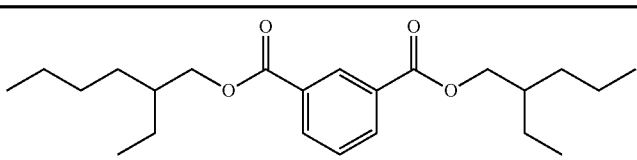 Bis(2-ethylhexyl) isophthalate | <0.1 | 0.15 | <0.1 |
| C$_7$H$_4$Cl$_2$O$_2$ | 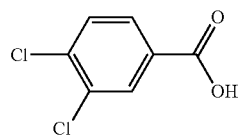 Dichlorobenzoic acid* | 1.43 | 1.04 | <0.1 |

*Only one of several possible isomers is shown.

The above-mentioned drug product samples were also analyzed for leachables by a validated HPLC method, EPH-006. EPH-006 was previously validated in terms of accuracy, precision, linearity and LOQ using Dichlorobenzoic Acid, Diethyl Phthalate (same functional class as Bis(2-ethylhexyl) Isophthalate), BPA and an Irganox related leachable. Dichlorobenzoic acid was also detected during the HPLC analysis using test method EPH-006 and the results are summarized in Table 35.

TABLE 35

DCBA Quantitation using EPH-006

| Lot | Amount of DCBA (µg/mL or ppm) by EPH-006 |
|---|---|
| 1 (Inverted) | 0.4 |
| 2 (Inverted) | 0.7 |
| 3 (Inverted) | <LOQ (0.1) |

The LOQ of the method was determined to be 0.1 ppm which is lower than the AET i.e., 0.15 ppm. The only compound detected above the LOQ level in the drug product samples was 2,4-Dichlorobenzoic acid or its possible isomer which is consistent with the LC-MS data. It is to be noted that dichlorobenzoic acid detected both by the MS study and the HPLC analysis was also detected previously during the leachable analysis of the 18M samples. Formation of DCBA may be attributed to possible interaction of benzoic acid with the chloride ions in the drug product formulation. The DCBA amount in drug product Lots 1 and 2 (manufactured using same API Siegfried Lot #16152015) is comparatively higher than that of Lot 3 (manufactured using different API Siegfried Lot #16152017). These results are in accordance with the previous results and further support our hypothesis that formation of DCBA may be attributable to interaction of benzoic acid with chloride ions during formulation of the ready-to-use ephedrine sulfate compositions consistent with the present disclosure.

To evaluate elemental impurities, three exhibit batches of Lots 1-3 of Example 2 stored in an inverted position for 24M at 25° C.±2° C. and 60%±5% RH were analyzed for Class 1 and 2A elements. The ICP-MS data is summarized below in Table 36.

TABLE 36

ICP-MS Results for Ready-to-Use Ephedrine Sulfate Composition Samples

| Element | Class | Parenteral PDE (µg/day) | PDE limits calculated based on 10 mL daily max. injection volume (ppb)* | ICP-MS Results (ppb): Lot 1 | ICP-MS Results (ppb): Lot 2 | ICP-MS Results (ppb): Lot 3 |
|---|---|---|---|---|---|---|
| Cadmium | 1 | 2 | 200 | <2.5 | <2.5 | <2.5 |
| Lead | 1 | 5 | 500 | <2.5 | <2.5 | <2.5 |
| Arsenic | 1 | 15 | 1500 | <2.5 | <2.5 | <2.5 |
| Mercury | 1 | 3 | 300 | 2.5 | <2.5 | <2.5 |
| Cobalt | 2A | 5 | 500 | <2.5 | <2.5 | <2.5 |
| Vanadium | 2A | 10 | 1000 | <2.5 | <2.5 | <2.5 |
| Nickel | 2A | 20 | 2000 | 7.0 | <2.5 | 3.6 |

*PDE value in ppb = Parental PDE value (µg/day) ÷ maximum daily volume (mL/day), i.e., 10 mL/day * 1000.

Conclusion

Extractables and leachables were identified using a combination of QTOF-GCMS and QTOF-LCMS-UV-CAD. Most of the identified extractables seem to be originating from the elastomeric components or additives. The same test methods were employed for extractables and leachables identification and relative-quantitation with an instrumental analytical evaluation threshold (AET) set at 0.1 µg/mL for LC-MS analysis and at 0.2 µg/mL for GC-MS analysis. During the leachables analysis a compound consistent with bis(2-ethylhexyl) isophthalate was detected in Ephedrine Sulfate Injection samples at a concentration of 0.15 µg/mL or lower by QTOF-GCMS. A compound consistent with dichlorobenzoic acid was detected in Ephedrine Sulfate Injection samples at a concentration of 1.43 µg/mL or lower by QTOF-LCMS-UV-CAD. Dichlorobenzoic acid was also found in HPLC analysis by EPH-006 with the amounts found at 0.7 µg/mL or lower. Formation of DCBA may be attributed to possible interaction of benzoic acid present in API with the chloride ions in the drug product formulation. Therefore, based on the data from this extractable and leachable study, the safety risk associated with leachables or elemental impurities in the ready-to-use ephedrine compositions consistent with the present disclosure appears to be low.

Further Examples

Further Example 1. A composition comprising ephedrine sulfate in water, wherein the ephedrine sulfate is present at a concentration of about 1 mg/mL to about 10 mg/mL.

Further Example 2. The composition of Further Example 1, wherein the ephedrine sulfate is present at a concentration of about 2 mg/mL to about 8 mg/mL.

Further Example 3. The composition of Further Example 1, wherein the ephedrine sulfate is present at a concentration of about 3 mg/mL to about 7 mg/mL.

Further Example 4. The composition of Further Example 1, wherein the ephedrine sulfate is present at a concentration of about 4 mg/mL to about 6 mg/mL.

Further Example 5. The composition of Further Example 1, wherein the ephedrine sulfate is present at a concentration of about 5 mg/mL.

Further Example 6. The composition of any preceding Further Example further comprising sodium chloride.

Further Example 7. The composition of Further Example 6, wherein the sodium chloride is present in an amount of about 9 mg/mL.

Further Example 8. The composition of any preceding Further Example, wherein the composition is stable when stored at 20° C. under light for at least 12 months.

Further Example 9. The composition of any preceding Further Example, wherein the composition does not include dextrose.

Further Example 10. The composition of any preceding Further Example, wherein the composition does not include benzyl alcohol.

Further Example 11. The composition of any preceding Further Example, wherein the composition consists essentially of ephedrine sulfate, sodium chloride and water.

Further Example 12. The composition of any preceding Further Example, wherein the composition consists of ephedrine sulfate, sodium chloride and water.

Further Example 13. The composition of any preceding Further Example, wherein the ephedrine sulfate is (−)-ephedrine sulfate.

Further Example 14. A sterile prediluted medicament comprising:
  about 3.8 mg/mL of ephedrine or an equimolar amount of an ephedrine salt;
  about 9 mg/mL sodium chloride; and
  water.

Further Example 15. The sterile prediluted medicament of Further Example 14, wherein the medicament does not include dextrose.

Further Example 16. The sterile prediluted medicament of Further Example 14 or Further Example 15, wherein the medicament does not include benzyl alcohol.

Further Example 17. The sterile prediluted medicament of any one of Further Examples 14 to 16, wherein a total volume of the medicament is about 10 mL.

Further Example 18. The sterile prediluted medicament of any one of Further Examples 14 to 17, wherein the medicament is housed in a vial.

Further Example 19. The sterile prediluted medicament of any one of Further Examples 14 to 18, wherein after storage at about 20° C. under light the medicament comprises at least 3 mg/mL of the ephedrine or an molar equivalent of the ephedrine salt.

Further Example 20. The sterile prediluted medicament of any one of Further Examples 14 to 19, wherein the ephedrine or ephedrine salt is ephedrine sulfate.

Further Example 21. The sterile prediluted medicament of Further Example 20, wherein the ephedrine sulfate is (−)-ephedrine sulfate.

Further Example 22. A ready-to-use unit dose form comprising:
 about 5 mg/mL of ephedrine sulfate;
 about 9 mg/mL of sodium chloride; and
 water.

Further Example 23. The ready-to-use unit dose form of Further Example 22, wherein the ready-to-use unit dose form is housed in a vial.

Further Example 24. The ready-to-use unit dose form of Further Example 22 or Further Example 23, wherein the ready-to-use unit dose form has a total volume of about 10 mL.

Further Example 25. The ready-to-use unit dose form of any one of Further Examples 22 to 24, wherein the ready-to-use unit dose form does not include dextrose.

Further Example 26. The ready-to-use unit dose form of any one of Further Examples 22 to 25, wherein the ready-to-use unit dose form does not include benzyl alcohol.

Further Example 27. The ready-to-use unit dose form of any one of Further Examples 22 to 26, wherein after storage at about 20° C. under light the ready-to-use unit dose form comprises at least 4 mg/mL of the ephedrine sulfate.

Further Example 28. A packaged pharmaceutical product comprising:
 a vial; and
 a solution housed within the vial,
  wherein the solution comprises, consists essentially of, or consists of:
   about 5 mg/mL of ephedrine sulfate;
   about 9 mg/mL sodium chloride; and
   water.

Further Example 29. The packaged pharmaceutical product of Further Example 28, wherein the solution has a total volume of about 10 mL.

Further Example 30. The packaged pharmaceutical product of Further Example 28 or Further Example 29, wherein the solution does not include dextrose.

Further Example 31. The packaged pharmaceutical product of any one of Further Examples 28 to 30, wherein the vial comprises, consists essentially of, or consists of glass.

Further Example 32. The packaged pharmaceutical product of any one of Further Examples 28 to 31, wherein the vial comprises, consists essentially of, or consists of polypropylene.

Further Example 33. The packaged pharmaceutical product of any one of Further Examples 28 to 32, wherein the solution is stable when stored at about 20° C. under light for at least 12 months.

Further Example 34. The packaged pharmaceutical product of Further Example 33, wherein after storage at about 20° C. under light for at least 12 months, the solution comprises ephedrine sulfate at a concentration of about 4 mg/mL to about 6 mg/mL.

Further Example 35. The packaged pharmaceutical product of Further Example 33, wherein after storage at about 20° C. under light for at least 12 months, the solution comprises at least 4 mg/mL of ephedrine sulfate.

Further Example 36. The packaged pharmaceutical product of Further Example 33, wherein after storage at about 20° C. under light for at least 12 months, the solution comprises at least 4.5 mg/mL ephedrine sulfate.

Further Example 37. The packaged pharmaceutical product of any one of Further Examples 28 to 36, wherein the ephedrine sulfate is (−)-ephedrine sulfate.

Further Example 38. A method of administering ephedrine sulfate to a subject in need thereof, the method comprising:
 drawing a composition comprising ephedrine sulfate from a sterile premixed pharmaceutical product into a syringe; and
 injecting the composition into the subject using the syringe,
 wherein the ephedrine sulfate is present in the composition in an amount of about 5 mg/mL.

Further Example 39. The method of Further Example 38, wherein the composition further comprises sodium chloride in an amount of about 9 mg/mL.

Further Example 40. The method of Further Example 38 or Further Example 39, wherein the composition further comprises water.

Further Example 41. The method of any one of Further Examples 38 to 40, wherein the composition does not include dextrose.

Further Example 42. The method of any one of Further Examples 38 to 41, wherein the method does not include diluting the sterile premixed pharmaceutical product before the step of injecting the composition into the subject using the syringe.

Further Example 43. The method of any one of Further Examples 38 to 42, wherein the composition housed within the vial of the sterile premixed pharmaceutical product is stable when stored at about 20° C. under light for at least 12 months.

Further Example 44. The method of Further Example 43, wherein after storage at about 20° C. under light for at least 12 months, the composition comprises ephedrine sulfate in an amount of about 4 mg/mL to about 6 mg/mL.

Further Example 45. The method of any one of Further Examples 38 to 44, wherein the ephedrine sulfate is (−)-ephedrine sulfate.

Further Example 46. A method of making a ready-to-use pharmaceutical composition comprising ephedrine or an ephedrine salt, the method comprising:
 combining ephedrine or an ephedrine salt, sodium chloride and water to provide a solution comprising:
  about 3.8 mg/mL ephedrine or an equimolar amount of an ephedrine salt, and
  about 9 mg/mL sodium chloride; and
 thereafter sterilizing the solution to provide a ready-to-use pharmaceutical composition comprising ephedrine or an ephedrine salt.

Further Example 47. The method of Further Example 46 further comprising placing the solution in one or more vials before the step of sterilizing.

Further Example 48. The method of Further Example 46 or Further Example 47, wherein the solution does not include dextrose.

Further Example 49. The method of any one of Further Examples 46 to 48, wherein the pharmaceutical composition is stable when stored at about 20° C. under light for at least 12 months.

Further Example 50. The method of Further Example 49, wherein after storage at about 20° C. under light for at least 12 months, the pharmaceutical composition comprises an amount of the ephedrine or the ephedrine salt that is at least 80% of the about 3.8 mg/mL ephedrine or the equimolar amount of the ephedrine salt.

Further Example 51. The method of any one of Further Examples 46 to 50, wherein the ephedrine or the ephedrine salt is ephedrine sulfate.

Further Example 52. The method of Further Example 51, wherein the ephedrine salt is (−)-ephedrine sulfate.

Further Example 53. The method of Further Example 51 or Further Example 52, wherein the equimolar amount of the ephedrine salt is about 5 mg/mL of the ephedrine sulfate.

Further Example 54. The method of any one of Further Examples 46 to 50, wherein the ephedrine or the ephedrine salt is ephedrine hydrochloride.

Further Example 55. The method of Further Example 54, wherein the ephedrine hydrochloride is (−)-ephedrine hydrochloride.

Further Example 56. The method of Further Example 54 or Further Example 55, wherein the equimolar amount of the ephedrine salt is about 4.6 mg/mL of the ephedrine hydrochloride.

Further Example 57. A method of treating hypotension in a subject in need thereof, the method comprising:
  drawing an effective amount of a packaged composition comprising ephedrine or an ephedrine salt into a syringe; and
  injecting the effective amount of the packaged composition into the subject in need thereof.

Further Example 58. The method of Further Example 57, wherein the packaged composition comprises ephedrine or an ephedrine salt in an amount equivalent to about 3.8 mg/mL ephedrine.

Further Example 59. The method of Further Example 57 or Further Example 58, wherein the packaged composition further comprises sodium chloride in an amount of about 9 mg/mL.

Further Example 60. The method of any one of Further Examples 57 to 59, wherein the packaged composition further comprises water.

Further Example 61. The method of any one of Further Examples 57 to 60, wherein the packaged composition does not include dextrose.

Further Example 62. The method of any one of Further Examples 57 to 61, wherein the method does not include diluting the packaged composition before the step of injecting the effective amount of the packaged composition into the subject in need thereof.

Further Example 63. The method of any one of Further Examples 57 to 62, wherein the packaged composition is stable when stored at about 20° C. under light for at least 12 months.

Further Example 64. The method of Further Example 63, wherein after storage at about 20° C. under light for at least 12 months, the packaged composition comprises ephedrine sulfate in an amount of about 4 mg/mL to about 6 mg/mL.

Further Example 65. The method of any one of Further Examples 57 to 64, wherein the ephedrine or ephedrine salt is (−)-ephedrine sulfate.

Further Example 66. The method of any one of Further Examples 57 to 65 further comprising determining a low blood pressure reading in the subject before the step of drawing the effective amount of the packaged composition comprising ephedrine or an ephedrine salt into the syringe.

Further Example 67. A method of increasing a blood pressure in a subject in need thereof, the method comprising:
  determining a low blood pressure reading associated with a subject;
  drawing about 1 mL to about 10 mL of a packaged composition comprising about 5.0 mg/mL ephedrine sulfate into a syringe; and
  injecting about 1 mL to about 10 mL of the packaged composition into the subject in need thereof,
  wherein the blood pressure reading associated with the subject increases after the step of injecting the packaged composition into the subject in need thereof, and
  wherein the method does not include diluting the packaged composition before the step of injecting the packaged composition into the subject in need thereof.

Further Example 68. The method of Further Example 67, wherein the packaged composition further comprises sodium chloride in an amount of about 9 mg/mL.

Further Example 69. The method of Further Example 67 or Further Example 68, wherein the packaged composition further comprises water.

Further Example 70. The method of any one of Further Examples 67 to 69, wherein the packaged composition does not include dextrose.

Further Example 71. The method of any one of Further Examples 67 to 70, wherein the method further comprises determining a second blood pressure reading associated with the subject after the step of injecting the packaged composition into the subject, wherein the second blood pressure reading is hypotensive.

Further Example 72. The method of Further Example 71 further comprising injecting about 1 mL to about 10 mL of the packaged composition into the subject after the step of determining the second hypotensive blood pressure reading associated with the subject.

Further Example 73. The method of any one of Further Examples 67 to 72, wherein the packaged composition is stable when stored at about 20° C. under light for at least 12 months.

Further Example 74. The method of Further Example 73, wherein after storage at about 20° C. under light for at least 12 months, the packaged composition comprises ephedrine sulfate in an amount of at least about 4 mg/mL.

Further Example 75. The method of Further Example 73, wherein after storage at about 20° C. under light for at least 12 months, the packaged composition comprises ephedrine sulfate in an amount of at least about 4.5 mg/mL.

Further Example 76. The method of any one of Further Examples 67 to 75, wherein the ephedrine sulfate is (−)-ephedrine sulfate.

Further Example 77. A ready-to-use packaged pharmaceutical composition comprising ephedrine or a pharmaceutically acceptable salt thereof, wherein the pharmaceutical composition exhibits no more than about 5% decrease in a concentration of the ephedrine or pharmaceutically acceptable salt thereof upon storage for at least 24 months.

Further Example 78. The ready-to-use packaged pharmaceutical composition of Further Example 77 further comprising sodium chloride.

Further Example 79. The ready-to-use packaged pharmaceutical composition of Further Example 77 or 78, wherein the ready-to-use packaged pharmaceutical composition is stored in a sealed glass container.

Further Example 80. The ready-to-use packaged pharmaceutical composition of any one of Further Examples 77-79, wherein the composition does not include dextrose.

Further Example 81. The ready-to-use packaged pharmaceutical composition of any one of Further Examples 77-80, wherein the composition does not include benzyl alcohol.

Further Example 82. The ready-to-use packaged pharmaceutical composition of any one of Further Examples 77-81, wherein the composition consists essentially of ephedrine or a pharmaceutically acceptable salt thereof, sodium chloride and water.

Further Example 83. The ready-to-use packaged pharmaceutical composition of any one of Further Examples 77-82 comprising about 5 mg/mL ephedrine sulfate.

Further Example 84. The ready-to-use packaged pharmaceutical composition of any one of Further Examples 77-82 comprising about 3.8 mg/mL ephedrine base.

Further Example 85. The ready-to-use packaged pharmaceutical composition of any one of Further Examples 77-84, wherein the ephedrine sulfate is (−)-ephedrine sulfate.

Further Example 86. The ready-to-use packaged pharmaceutical composition of any one of Further Examples 77-85, wherein the composition is formulated as a total volume of about 10 mL.

CONCLUSION

Unless otherwise specified or required by context, the term "ephedrine" as used herein refers to (−)-ephedrine (i.e., (1R,2S)-2-methylamino-1-phenylpropan-1-ol sulfate).

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

It is to be understood that both the foregoing descriptions are exemplary and explanatory only, and are not restrictive of the methods and devices described herein. In this application, the use of the singular includes the plural unless specifically stated otherwise. Also, the use of "or" means "and/or" unless stated otherwise. Similarly, "comprise," "comprises," "comprising," "include," "includes" and "including" are not intended to be limiting.

All patents, patent applications, publications, and references cited herein are expressly incorporated by reference to the same extent as if each individual publication or patent application was specifically and individually indicated to be incorporated by reference.

What is claimed is:

1. A method of making a shelf-stable, ready-to-use ephedrine sulfate composition, the method comprising:
    combining ephedrine sulfate, sodium chloride or dextrose, and water to form a batch solution comprising an initial ephedrine sulfate level of 5 mg/mL, 9 mg/mL sodium chloride or 5% dextrose, and no preservative;
    optionally contacting the batch solution with an acid or a base to obtain an initial pH level of the solution of 4.5 to 7;
    filtering the batch solution through a membrane filter to obtain a filtered batch solution;
    sanitizing one or more containers;
    placing not more than 20 mL of the filtered batch solution into one of the one or more sanitized containers to obtain one or more filled containers;
    sealing each filled container to obtain sealed containers including a shelf-stable, ready-to-use ephedrine sulfate composition; and
    maintaining a pH level of the shelf-stable, ready-to-use ephedrine sulfate composition in the sealed containers that is within 0.5 pH units of the initial pH level during storage at 25° C. and 60% relative humidity for at least 12 months or during storage at 40° C. and 75% relative humidity for at least 6 months.

2. The method of claim 1, wherein the shelf-stable, ready-to-use ephedrine sulfate composition has, after the step of maintaining, a bacterial endotoxin level of not more than 7 EU/mg.

3. The method of claim 1, wherein the shelf-stable, ready-to-use ephedrine sulfate composition has, after the step of maintaining, an ephedrine level within 5% of the initial ephedrine sulfate level.

4. The method of claim 1, wherein the shelf-stable, ready-to-use ephedrine sulfate composition has, after the step of maintaining, a level of (+)-1S,2R-ephedrine of not more than 0.5%.

5. The method of claim 1, wherein the shelf-stable, ready-to-use ephedrine sulfate composition has, after the step of maintaining, a level of total impurities of not more than 0.75%.

6. The method of claim 1, wherein the shelf-stable, ready-to-use ephedrine sulfate composition has, after the step of maintaining, a level of any one unknown individual impurity of not more than 0.2%.

7. The method of claim 1, wherein the shelf-stable, ready-to-use ephedrine sulfate composition has, after the step of maintaining, not more than 6000 particles greater than or equal to 10 μm in size per container.

8. The method of claim 1, wherein the shelf-stable, ready-to-use ephedrine sulfate composition has, after the step of maintaining, not more than 600 particles greater than or equal to 25 μm in size per container.

9. The method of claim 1 further comprising a step of sterilizing the solution before the step of maintaining.

* * * * *